(12) United States Patent
Jukarainen et al.

(10) Patent No.: US 6,476,079 B1
(45) Date of Patent: *Nov. 5, 2002

(54) DEVICES FOR THE DELIVERY OF DRUGS HAVING ANTIPROGESTINIC PROPERTIES

(75) Inventors: Harri Jukarainen, Turku (FI); Tommi Markkula, Cheshire (GE); Juha Ala-sorvari, Turku (FI); Matti Lehtinen, Piispanristi (FI); Jarkko Ruohonen, Vanhalinna (FI)

(73) Assignee: Leiras Oy, Turku (FI)

( * ) Notice: Subject to any disclaimer, the term of this patent is extended or adjusted under 35 U.S.C. 154(b) by 0 days.

This patent is subject to a terminal disclaimer.

(21) Appl. No.: 09/472,126

(22) Filed: Dec. 23, 1999

(51) Int. Cl.$^7$ .................. A16K 47/32; A16K 13/00; A16K 2/00; A16K 9/14
(52) U.S. Cl. .................. 514/772.4; 514/843; 424/422; 424/423; 424/424; 424/486
(58) Field of Search .................. 524/862, 865; 424/423, 424, 422, 473, 486, 449; 514/170, 772.4, 171, 179, 843, 899

(56) References Cited

U.S. PATENT DOCUMENTS

| | | | |
|---|---|---|---|
| 3,279,996 A | * 10/1966 | Long, Jr. et al. | 424/424 |
| 3,832,252 A | * 8/1974 | Higuchi et al. | 424/424 |
| 3,836,560 A | 9/1974 | Prokai et al. | 260/448.8 R |
| 4,155,991 A | * 5/1979 | Schopflin et al. | 424/15 |
| 4,323,488 A | 4/1982 | Takago et al. | 528/32 |
| 4,600,751 A | 7/1986 | Lee et al. | 525/404 |
| 4,621,029 A | * 11/1986 | Kawaguchi | 524/862 |
| 4,814,184 A | * 3/1989 | L.M.J. Aguadisch et al. | 424/424 |
| 5,521,166 A | * 5/1996 | Grubb | 514/170 |
| 5,767,193 A | * 6/1998 | Fujiki et al. | 524/862 |
| 5,811,487 A | * 9/1998 | Schulz, Jr. et al. | 524/862 |
| 5,889,108 A | 3/1999 | Zhang | 524/862 |
| 6,063,395 A | * 5/2000 | Markkula et al. | 424/422 |
| 6,013,711 A | 9/2000 | Lewis et al. | 524/265 |

FOREIGN PATENT DOCUMENTS

| | | |
|---|---|---|
| EP | 0 545 002 | 6/1993 |
| EP | 0 882 753 | 12/2000 |
| FI | 973 427 | 2/1999 |
| WO | WO 00/00550 | 1/2000 |

OTHER PUBLICATIONS

Hans W. haesslin, et al., "Dimethylsiloxane–ethylene oxide block copolymers, 1, microphase separation of low segment mass copolymers and their compatibility with water and oil", 185 *makromol, Chem.* 2625–2645 (1984).

Hans W. haesslin, "Dimethylsiloxane–ethylene oxide block copolymers 2, Preliminary results on dilute solution properties", 186 *Makromol. Chem.* 357–366 (1985).

Chemical Abstracts 126: 2000090, "Synthesis and Drug Release Property of Polysiloxane Containing Pendant Long Alkyl Ether Group" (1997).

ulman, et al., "Drug Permeability of Modified Silicone Polymers. I. Silicone –Organic Block Polymers", 10 *J. Controlled Release* 251–260 (1989).

(List continued on next page.)

Primary Examiner—Thurman K. Page
Assistant Examiner—Blessing Fubara
(74) Attorney, Agent, or Firm—James C. Lydon

(57) ABSTRACT

A device for the controlled release over a prolonged period of time of a drug having antiprogestinic properties, the device including a core containing the drug, optionally a membrane encasing the core, where at least one of the core and membrane, when present, is made of a siloxane-based elastomer composition including at least one elastomer and optionally a non-crosslinked polymer. The device is characterized in that the elastomer composition includes poly (alkylene oxide) groups and that the poly(alkylene oxide) groups are present in the elastomer or polymer as alkoxy-terminated grafts of polysiloxane units, or as blocks, the grafts or blocks being linked to the polysiloxane units by silicon-carbon bonds, or as a mixture of these forms.

15 Claims, 5 Drawing Sheets

OTHER PUBLICATIONS

Loth, et al., "Methoxy–polyethoxy side–chain silastomers as materials controlling drug delivery by diffusion flux", 54 *J. Controlled Release* 273–282 (1998).

Trofimov, et al, "Polyethylene oxide–polysiloxane branched copolymers and networks. 1. Hydropsilylation of vinyl ethers of oligoethylene glycols with polyhydridosiloxanes", 8 *Russian Chemical Bulletin* 463–469 (1999).

Yang et al., "Synthesis and Characterization of polymethylsiloxane/poly (ethyleneglycol) monomethyl ether copolymers", 17 *J. Ch. Colloid & Interface Soc.* 19–28 (1994).

Akimoto et al., "Polymeric percutaneous drug penetration enhancer Synthesis and enhancing property of PEG/PDMS block copolymer with a cationic end group", 49 *J. Controlled Release* 229–241 (1997).

Yunhua et al., "The Synthesis and Drug Release Property of Polysiloxane Bearing Pendant Long Alkyl Ether Group", 1 *Acta Polymerica Sinica* 62–67 (1997).

\* cited by examiner

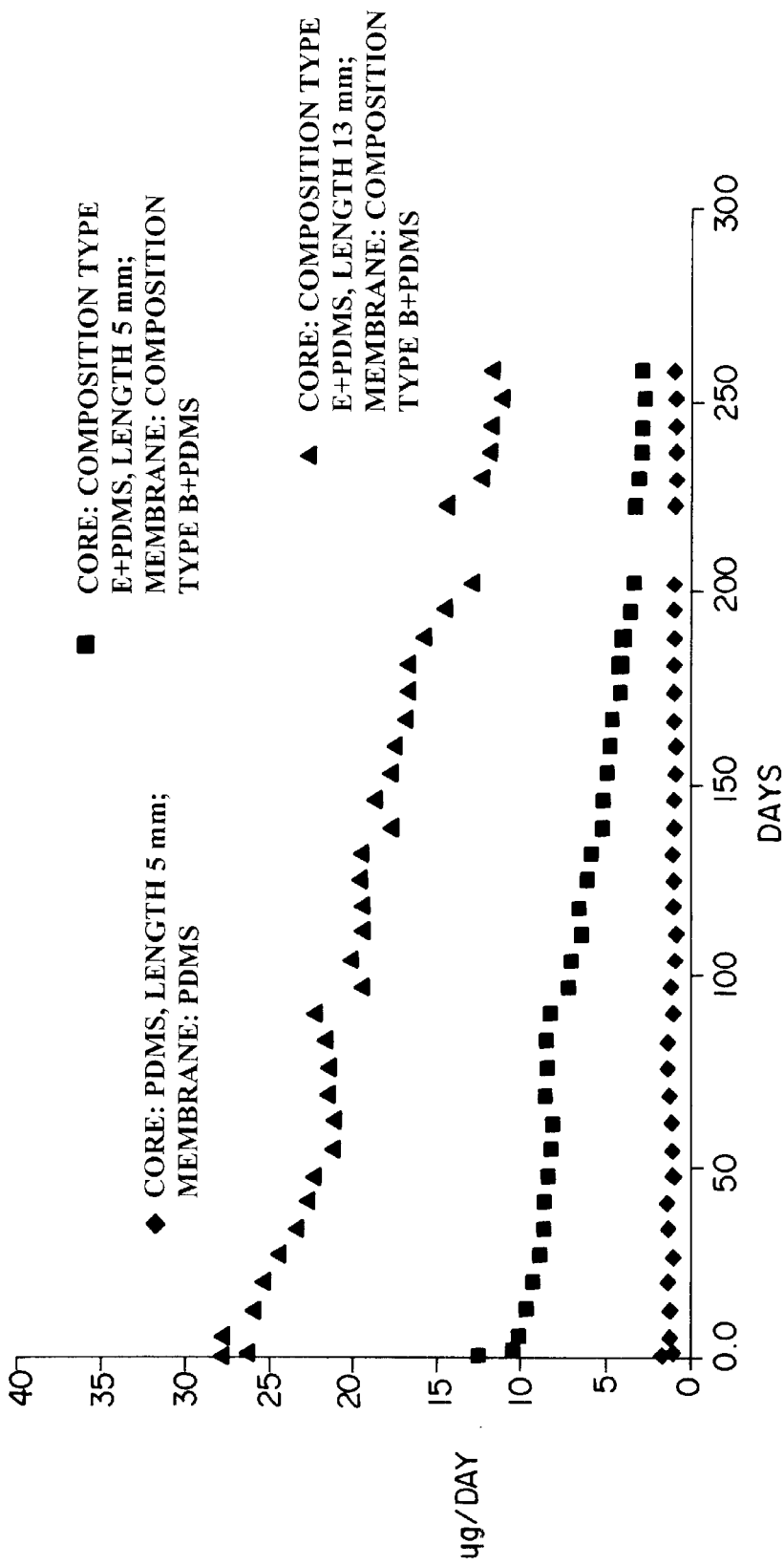

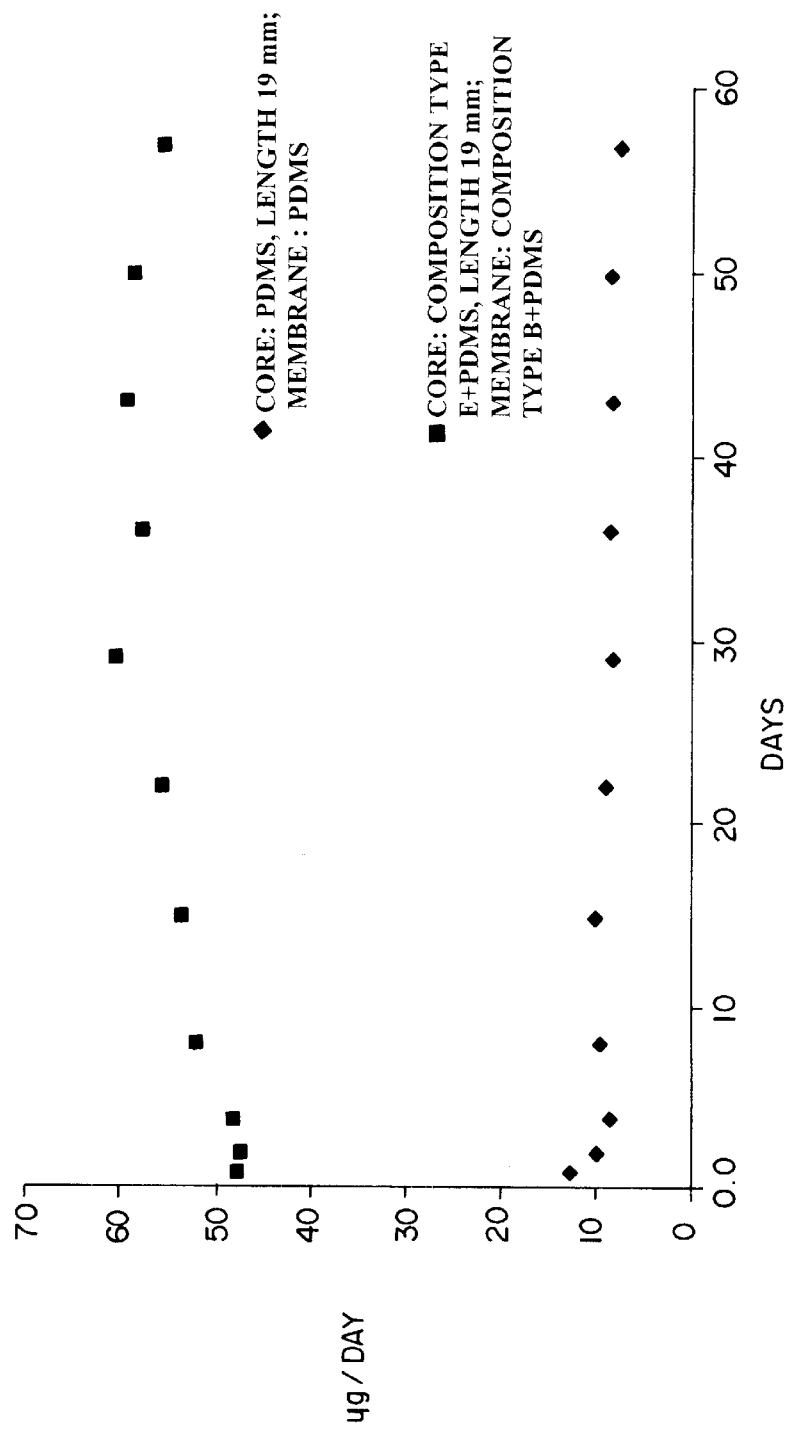

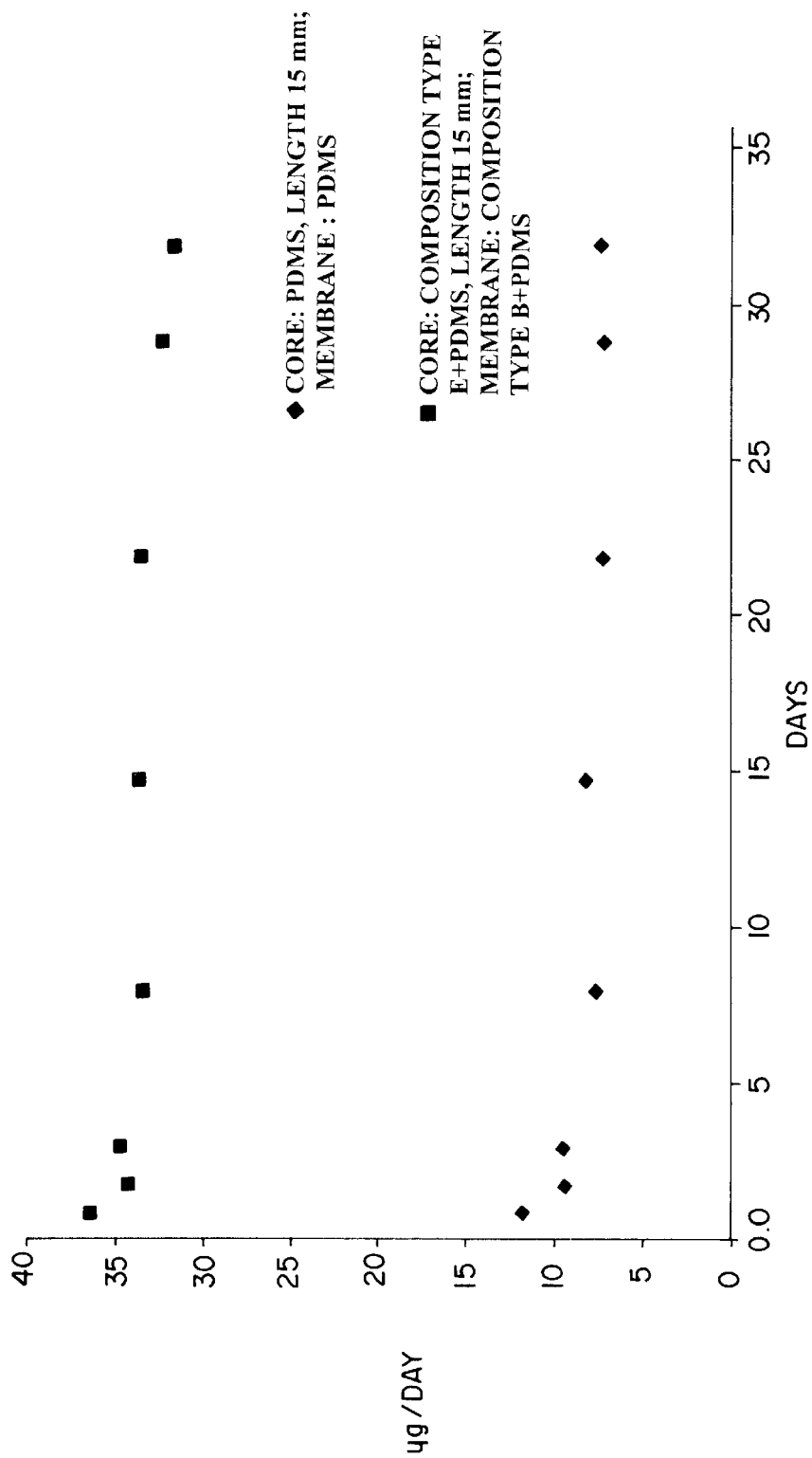

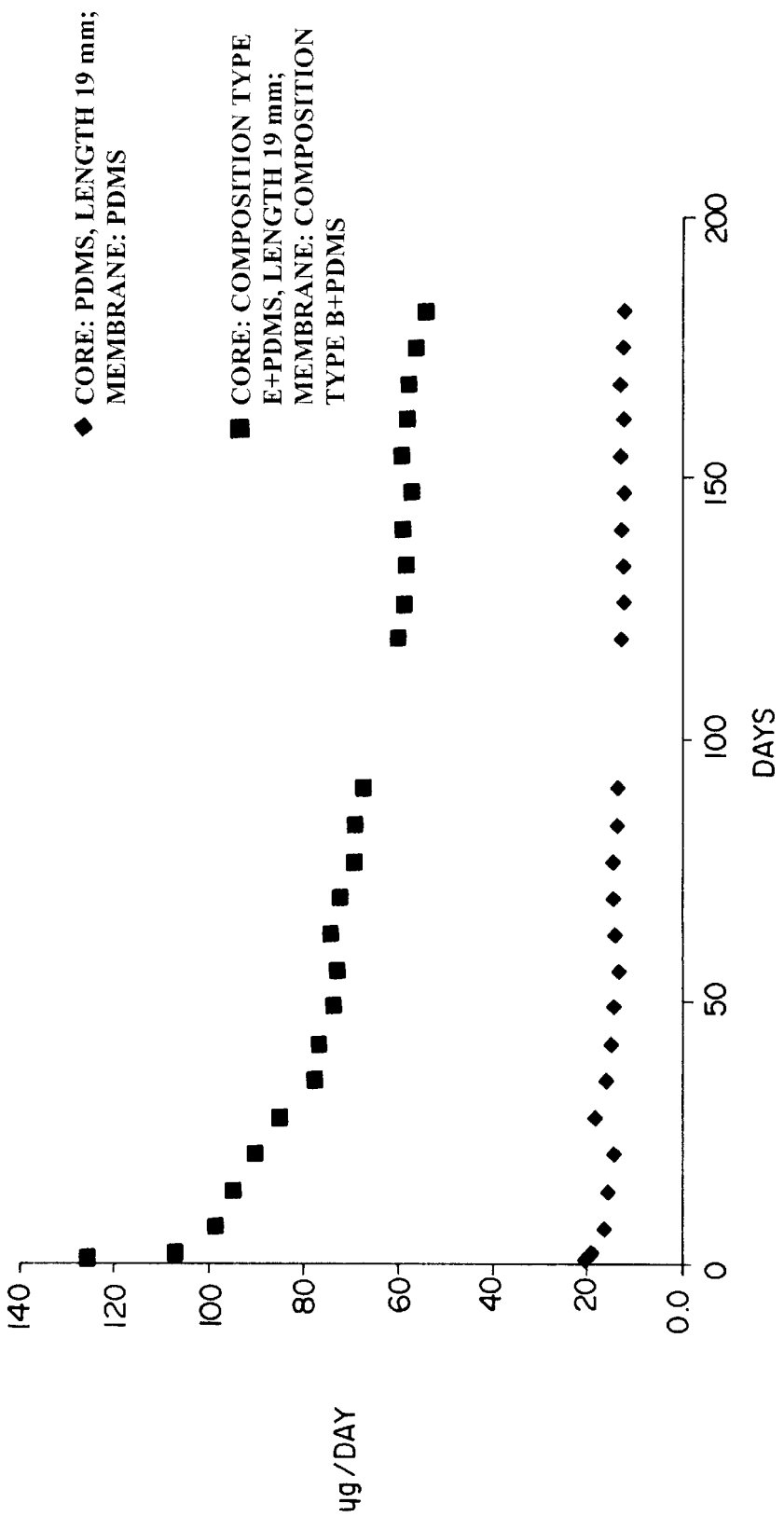

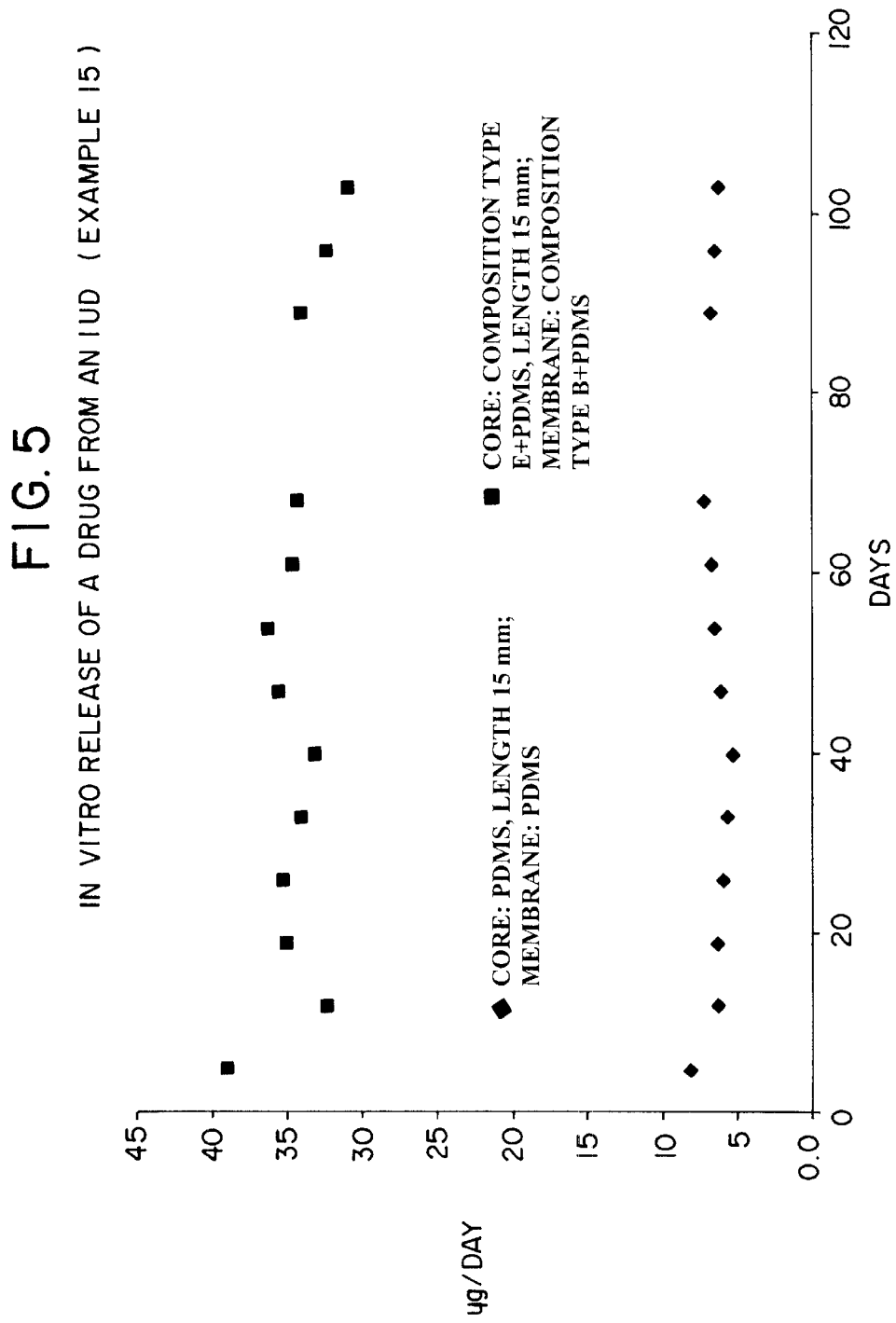

DEVICES FOR THE DELIVERY OF DRUGS HAVING ANTIPROGESTINIC PROPERTIES

FIELD OF THE INVENTION

This invention relates to devices for the controlled release of drugs having antiprogestinic properties, particularly to implantable devices, intrauterine or intravaginal devices, or transdermal devices for the administration of said drug at a desirable rate over a prolonged period of time.

BACKGROUND OF THE INVENTION

The publications and other materials used herein to illuminate the background of the invention, and in particular, cases to provide additional details respecting the practice, are incorporated by reference.

The use of drug delivery devices, which provide for the slow release of a drug to the body at a controlled rate over a prolonged period of time to achieve a desired physiological or pharmacological effect, his proved beneficial in many therapeutic areas. A principal advantage of employing sustained-release compositions is that many therapeutic agents would otherwise be rapidly metabolised or cleared from the patient's system thus necessitating frequent administration of the drag to maintain a therapeutically effective concentration.

A variety of methods have been described in the literature, including the physiological modification of absorption or excretion, modification of the solvent, chemical modification of the drug, absorption of drug on an insoluble carrier, use of suspensions and implantation pellets. Other methods include mixing the drug with a carrier such as waxes, oils, fats, and soluble polymers, which are gradually disintegrated by the environment resulting in release of the drug. Much attention has been directed to the reservoir type of device, i.e., a device in which a drug is encased within a polymeric container, with or without a solvent or carrier, which allows passage of drug from the reservoir.

Still another type of drug delivery device is the type in which a drug is dispersed in a polymer and from which the drug is released either by degradation of the polymer or by passage of the drug through the polymer membrane.

In principle any polymer can be used as a carrier as long as it is biocompatible. However, the release kinetics of a drug from a polymeric delivery system depend on the molecular weight, solubility, diffusivity, and charge of the active substance as well as the characteristics of the polymer, the percentage of drug loading, the distance the drug must diffuse through the device body to reach its surface and the characteristics of any matrix or membrane coating. The importance of these factors coupled with the specific pharmacology, toxicology, and therapeutic goals necessitate that the design of a polymeric device for a specific agent must be carefully constructed.

Examples of commonly used polymeric materials include elastomers such as polysiloxanes, ethylene/vinyl acetate copolymers (EVA), and copolymers of dimethylsiloxanes and methylvinylsiloxanes. The structural integrity of the material may be enhanced by the addition of a particulate material such as silica or diatomaceous earth.

Devices manufactured from EVA suffer from certain drawbacks. The materials are rather stiff and non-flexible and are therefore rather inconvenient to wear as implants beneath the skin.

Polysiloxanes, in particular poly(dimethyl siloxane) (PDMS), are highly suitable for use as a membrane or matrix regulating the permeation rate of drugs in various drug forms, in particularly in implants, intrauterine devices and vaginal rings.

Polysiloxanes are physiologically inert, and a wide group of drugs are capable of penetrating polysiloxane membranes, which also have the required strength properties.

It is known from the literature that adding of poly (ethylene oxide) groups, i.e. PEO groups to a PDMS polymer may increase the permeation rate of the drugs. Publication Ullman et al. Journal of Controlled Release 10 (1989) 251–260 describes membranes from a block copolymer which contains PEO and PDMS and the penetration of various steroids through these membranes. It is noted that an increasing PEO amount in the block polymer tends to increase the penetration of hydrophilic steroids, while the penetration of lipophilic steroids decreases. However, the block copolymer described in the publication is very complicated in its structure and preparation and would therefore not be facile in more extensive technical production.

Contraceptive subcutaneous implants are known in the art and they are described e.g. in U.S. Pat. Nos. 4,957,119, 5,088,505, 5,035,891, 5,565,443 and 5,633,000. Implants of the matrix type produced from polydimethyl siloxanes are described in the literature (Nash, Robertson and coworkers, Contraception 18, 1978, 367).

The commercially available Norplant® system is an implant having a core containing the synthetic progestin, levonorgestrel as the active substance, and where the core is surrounded by a membrane of a silicone elastomer of poly(dimethylsiloxane). A special preparation of this kind is Jadelle® in which the core is a poly(dimethylsiloxane) based matrix with levonorgestrel dispersed therein. The membrane is an elastomer made from PDMS and silica filler, which, besides giving necessary strength properties to the membrane also retards the permeation of the active agent through the membrane.

U.S. Pat No. 3,279,996 (Long et al.) describes an implant which contains an active substance encased by a polysiloxane membrane.

Dutch Patent No. 167,850 (Zaffaroni) describes an implant, in which the active substance is contained in a polymer and this polymer loaded with active substance is encased by a polymer membrane, which completely controls the release rate. However, the dimensions, the degree of rigidity and the release duration of the contraceptive substance for these implants are not practical.

U.S. Pat. No. 3,854,480 describes a drug delivery device, e.g. an implant, for releasing a drug at a controlled rate for a prolonged period of time. The device has a core matrix in which the drug is dispersed. The core is surrounded by a membrane, that is insoluble in body fluids. The core matrix as well as membrane are permeable to the drug by diffusion. The materials of the core and membrane are chosen so that the drug diffuses through the membrane at a lesser rate than through the core matrix. Thus the membrane controls the release rate of the drug. As a suitable polymer for the core matrix is mentioned poly(dimethyl siloxane) and as suitable polymers for the membrane are mentioned polyethylene and a copolymer of ethylene and vinyl acetate (EVA).

U.S. Pat. No. 5,660,848 discloses a subdermally implantable drug-delivery device, which contains a central core extending in an anal direction and having an outer surface and opposing ends. The core includes a matrix with a therapeutically effective amount of a subdermally administrable drug substantially uniformly dispersed in a polymeric base material; an intermediate polymeric layer overlying the outer surface of the central core; and an outer polymeric layer overlying the intermediate layer, wherein the intermediate layer controls the rate of diffusion of the drug from the central core to the outer layer. In preferred embodiments, the drug is a contraceptive agent; the polymeric base material and the outer polymeric layer each contain a polydimethylsiloxane and the intermediate layer contains a porous material such as cellulose.

Numerous types of vaginal rings have been described in the patent and non-patent literature like, e.g., U.S. Pat. Nos. 4,012,496 and 4,155,991 (both to Schopflin et al.), U.S. Pat. No. 4,292,965 (Nash), U.S. Pat. No. 3,545,439 (Duncan), U.S. Pat. No. 3,920,805 (Roseman), U.S. Pat. Nos. 3,991,760 and 3,995,634 both to Drobish et al.), U.S. Pat. No. 3,995,633 (Gougen), U.S. Pat. Nos. 4,250,611 and 4,286,587 (both to Wong), U.S. Pat. No. 4,596,576 (de Nijs); WO95/00199 (Lehtinen et al.), Contraception 19:507–516 (1979), (Jackanicz).

Implants or intravaginal devices for administration of antiprogestins have generally been disclosed e.g. in U.S. Pat. Nos. 5,516,769, 5,521,166, 5,439,913, 5,622,943 and 5,681,817.

OBJECT AND SUMMARY OF THE INVENTION

The object of this invention is to provide a device for the delivery of certain drugs having antiprogestinic properties for the administration of said drugs at a desirable rate over a prolonged period of time.

The object of this invention is especially to provide a drug delivery device in the form of an implant, intravaginal device, intracervical or intrauterine device or transdermal patch intended for the administration of said drug.

The object is particularly to provide a flexible and smooth drug releasing device, which has a small cross section and which is easy to insert and convenient to wear.

Furthermore, the object is particularly to provide a device with which the release rate of the drug easily can be adjusted to a desirable level.

The invention is based on the fact that elastomer compositions with poly(alkylene oxide) groups in the polysiloxane release the active agent at a greater rate than polysiloxanes without such groups. A desirable delivery rate of the active agent can thus be achieved by the use of an elastomer composition (as matrix or membrane or both) having a proper amount of poly(alkylene oxide) groups.

Thus, the present invention concerns a device for the controlled release over a prolonged period of time, of a drug having antiprogestinic properties, said device comprising a core comprising said drug, optionally a membrane encasing said core, wherein said core and/or membrane is made of a siloxane-based elastomer composition comprising at least one elastomer and possibly a non-crosslinked polymer. According to the invention, the elastomer composition comprises poly(alkylene oxide) groups, wherein the poly(alkylene oxide) groups are present in the elastomer or polymer as alkoxy-terminated grafts of polysiloxane units, or as blocks, the said grafts or blocks being linked to the polysiloxane units by silicon-carbon bonds. The elastomer composition can also be a mixture of the aforementioned forms.

BRIEF DESCRIPTION OF THE DRAWINGS

FIG. 1 shows the daily in vitro release of an antiprogestin from the implants described in Example 11 (diamonds: 5 mm long core based on PDMS; squares: 5 mm long core based on the new elastomer composition, and triangles: 13 mm long core based on the new elastomer composition).

FIG. 2 shows the daily in vitro release of an antiprogestin from the IUD:s described in Example 12 (diamonds: 19 mm long core based on PDMS; squares: 19 mm long core based on the new elastomer composition).

FIG. 3 shows the daily in vitro release of an antiprogestin from the implants described in Example 13 (diamonds: 15 mm long core based on PDMS; squares: 15 mm long core based on the new elastomer composition).

FIG. 4 shows the daily in vitro release of an antiprogestin from the IUD:s described in Example 14 (diamonds: 19 mm long core based on PDMS; squares: 19 mm long core based on the new elastomer composition).

FIG. 5 shows the daily in vitro release of an antiprogestin from the IUD:s described in Example 15 (diamonds: 15 mm long core based on PDMS; squares: 15 mm long core based on the new elastomer composition).

DETAILED DESCRIPTION OF THE INVENTION

General Description of the Elastomer Composition

The term "elastomer composition" may stand for one single elastomer, in which case the polysiloxane units which contain poly(alkylene oxide) groups are present in the said elastomer.

According to another embodiment, the elastomer composition may be made up of two elastomers which are interlaced, one inside the other. In this case the first elastomer comprises poly(alkylene oxide) groups so that the poly(alkylene oxide) groups are present in the said elastomer either as alkoxy-terminated grafts of polysiloxane units or as blocks, the said grafts or blocks being linked to the polysiloxane units by silicon-carbon bonds. The poly(alkylene oxides) may also be present as a blend of the options mentioned. The second elastomer may be a siloxane-based elastomer, suitably a poly(dimethyl siloxane)-based elastomer. The said second elastomer may possibly also comprise poly(alkylene oxide) groups.

These poly(alkylene oxide) groups may also be present either as alkoxy-terminated grafts of poly(dimethyl siloxane) units or as blocks, the said grafts or blocks being linked to the poly(dimethyl siloxane) units by silicon-carbon bonds. The poly(alkylene oxides) may also in this elastomer be present as a blend of the options mentioned above.

According to a third embodiment, the elastomer composition may be a blend which comprises a siloxane-based elastomer, which is, for example, made up of PDMS, and at least one linear polysiloxane copolymer which comprises poly(alkylene oxide) groups. In his case the poly(alkylene oxide) groups are present in the said polymer either as alkoxy-terminated grafts of polysiloxane units or as blocks, the said grafts or blocks being linked to the polysiloxane units by silicon-carbon bonds. The poly(alkylene oxide) groups may, of course, also be present in the polymer as a blend of the forms mentioned. In this embodiment also the siloxane-based elastomer may comprise poly(alkylene oxide) groups, in which case these poly(alkylene oxide) groups are present in the elastomer either as alkoxy-terminated grafts of polysiloxane units or as blocks, the said blocks or grafts being linked to the polysiloxane units by silicon-carbon bonds. The poly(alkylene oxide) groups may also be present as a blend of the forms mentioned.

Of course, the elastomer composition may also be made up of two elastomers interlaced one inside the other, as above, and at least one linear polysiloxane copolymer which comprises poly(alkylene oxide) groups.

The poly(alkylene oxide) groups of the elastomer composition may suitably be, for example, poly(ethylene oxide) groups (PEO groups).

The polysiloxane units of the elastomer composition are preferably groups having the formula $$-(SiR'R''O)_q SiR'R''-$$

where some of the substituents R' and R'' are
  free groups, which are the same or different and which are a lower alkyl group, or a phenyl group, in which case the said alkyl or phenyl groups may be substituted or unsubstituted, or alkoxy-terminated poly(alkylene oxide) groups having the formula $R_3$—O—(CRH—$CH_2$—O)$_m$—alk, where alk is a lower alkyl group, suitably methyl, R is hydrogen or a lower alkyl, m is 1 . . . 30, and $R_3$ is a straight or branched $C_2$–$C_6$ alkylene group,
  bonds, formed from the hydrogen or alkenyl groups, to other polymer chains in the elastomer, and
  optionally unreacted groups, such as hydrogen, vinyl or vinyl-terminated alkenyl, and
  q is 1 . . . 3000.

The term "lower alkyl" stands here and generally in the description of the elastomer composition for $C_1$–$C_6$ alkyl groups.

The above-mentioned free R' and R'' groups are suitably a lower alkyl group, preferably methyl.

The term "poly(alkylene oxide) group" means that said group comprises at least two alkyl ether groups successively connected to each other.

According to a preferred embodiment, the poly(alkylene oxide) groups are present in the elastomer in the form of poly(alkylene oxide) blocks having the formula $$-(CH_2)_y O(CRHCH_2O)_m(CH_2)_y-,$$

or $$-CH_2CR_1HCOO(CRHCH_2O)_m COCR_1HCH_2-$$

where
  R is hydrogen, a lower alkyl or a phenyl,
  $R_1$ is hydrogen or a lower alkyl, y is 2 . . . 6, and m is 1 . . . 30.

The elastomer composition suitably contains a filler, such as silica, in order that the membrane should obtain a sufficient strength.

The word "membrane" means the same as film.

General Description of the Method for the Preparation of the Elastomer Composition According to a preferred embodiment the novel elastomer is prepared by crosslinking, in the presence of a catalyst, a vinyl-functional polymer component and a hydride-functional siloxane component.

By crosslinking is meant the addition reaction of the hydride-functional siloxane component with the carbon-carbon double bond of the vinyl-functional polymer component.

According to another embodiment, the elastomer is prepared by crosslinkig the polymer in the presence of a peroxide catalyst. In this case the vinyl and methyl groups react with each other and form carbon-carbon bonds. A crosslink may also be formed between two methyl groups or between two vinyl groups.

For crosslinking, the amounts of the components are preferably selected so that the ratio of the molar amounts of the reactive hydrides and the reactive double bonds is at least 1.

The vinyl-functional polymer component may be
a) a vinyl-functional polysiloxane having the formula $$R'-SiR'R''O(SiR'R''O)_r SiR'R''R'$$

where R' and R'' are the same or different, and are a lower alkyl group, or a phenyl group, in which case the said alkyl or phenyl group may be substituted or unsubstituted, and where some of the substituents R' and/or R'' have been substituted for by vinyl groups, and r is 1 . . . 27000, or b) an alkenyl terminated polysiloxane-based block copolymer having the formula $$T(AB)_x AT \qquad (I),$$

where
  $A=-(SiR'R''O)_q SiR'R''-$, where R' and R'' are the same or different and are a lower alkyl group, or a phenyl, in which case the said alkyl or phenyl group may be substituted or unsubstituted;
  B is a poly(alkylene oxide) having the formula $$-R_3O(CRHCH_2O)_m R_4-,$$

or $$-CH_2CR_1HCOO(CRHCH_2O)_m COCR_1HCH_2-$$

and T is $$R^{11}O(CRHCH_2O)_m R_3-,$$

or $$CH_2=CR_1COO(CRHCH_2O)_m COCR_1HCH_2-$$

where
  R is hydrogen, a lower alkyl or phenyl, $R_1$ is hydrogen or a lower allyl, $R_3$ and $R_4$ are the same or different and are linear or branched $C_2$–$C_6$ alkylene groups,
  $R^{11}$ is a linear or branched $C_2$–$C_6$ alkenyl group, m is 1 . . . 30, q is 1 . . . 3000, and
  x is 0 . . . 100, or c) a vinyl-functional polysiloxane random or block copolymer having the formula $$R'-SiR'R''O(SiR'R''O)_r(SiR'R''O)_p SiR'R''-R'$$

where in the first repeat unit R' and R'' are the same or different and are a lower alkyl group, or a phenyl group, in which case the said alkyl or phenyl group may be substituted or unsubstituted, and where some of the substituents R' and/or R'' have been substituted for by vinyl groups, and r is 1 . . . 27000, and
  where in the second repeat unit R' is a lower alkyl group, or an alkoxy-terminated poly(alkylene oxide) group having the formula
  $-R_3$—O—(CRH—$CH_2$—O)$_m$-alk, where alk is a lower alkyl group, suitably methyl, R is hydrogen or a lower alkyl group, $R_3$ is a straight or branched $C_2$–$C_6$ alkylene, and m is 1 . . . 30, or R' is a phenyl group, in which case the said alkyl or phenyl group may be substituted or unsubstituted, and R'' is a lower alkyl or a phenyl group, in which case the said alkyl or phenyl group may be substituted or unsubstituted, and p is 1 . . . 5000, or d) α,ω-dialkenyl poly(alkylene oxide) having the formula $$R^{11}-O-(CRHCH_2O)_m-R^{12}$$

where $R^{11}$ and $R^{12}$ are the same or different linear or branched $C_2-C_6$ alkenyl groups, R is hydrogen or a lower alkyl and m is 1 ... 30, or e) a blend of at least two of the above-mentioned components a)–d).

If the formula of the vinyl-functional polysiloxane copolymer is, in accordance with the above description, R'—SiR'R"O(SiR'R"O)$_x$(SiR'R"O)$_p$SiR'R"—R', it should be noted that the formula is a kind of gross formula, in which the blocks in successive parentheses may appear in any order in relation to one another. Furthermore, it is preferable that both a vinyl group and the above-mentioned alkoxy-terminated poly(alkylene oxide) group are not bonded to one and the same Si atom.

The hydride-functional component may be a) a hydride-functional siloxane, which may be linear, star shaped, branched or cyclic, or b) a hydride-terminated siloxane-based block copolymer having the formula $$T(BA)_xBT \quad (II),$$

where
T=H—SiR'R"O(SiR'R"O)$_q$SiR'R"—,
A=—SiR'R"O(SiR'R"O)$_q$SiR'R"—, where R' and R" are the same or different and are a lower alkyl group or a phenyl group, in which case the said alkyl or phenyl group may be substituted or unsubstituted;
B is a poly(alkylene oxide) having the formula $$-R_3-O(CRHCH_2O)_mR_4-,$$

or $$-CH_2CR_1HCOO(CRHCH_2O)_mCOCR_1HCH_2-$$

where R is hydrogen, a lower alkyl or a phenyl, $R_1$ is hydrogen or a lower alkyl, $R_3$ and $R_4$ are the same or different and are linear or branched $C_2-C_6$ alkyl groups, m is 1 ... 30, q is 1 ... 3000, and x is 0 ... 100, or c) a blend of the above-mentioned components a) and b).

According to one embodiment, the hydride-functional siloxane copolymer may be linear, in which case its formula is $$R'-SiR'R"O(SiR'R"O)_rSiR'R"R'$$

where R' and R" are the same or different and are a lower alkyl group, or a phenyl group, in which case the said alkyl or phenyl group may be substituted or unsubstituted, and where some of the substituents R' and/or R" have been substituted for by hydrogen, and r is 1 ... 27000.

The vinyl-functional polymer component may contain a filler, suitably silica.

The catalyst to be used in the crosslinking is suitably a noble metal catalyst, most commonly a platinum complex in alcohol, xylene, divinyl siloxane or cyclic vinyl siloxane. An especially suitable catalyst is a Pt(0)-divinyl-tetramethyl disiloxane complex.

The elastomer composition made up of two elastomers is prepared so that initially a first elastomer is formed, whereafter a second elastomer is formed by crosslinkg in the presence of the first elastomer. Thus the second elastomer will penetrate through the first elastomer.

The elastomer composition which comprises an elastomer and a linear polymer is prepared, for example, by blending a vinyl-functional polymer component, a hydride-functional component, and a polymer which has no vinyl or hydride groups. In the crosslinking, the vinyl-functional polymer component and the hydride-functional component form an elastomer, but the polymer component which does not contain the said functional groups will not take part in the crosslinking reaction but will remain, in a non-crosslinked form inside the elastomer.

Different Types of Devices

The device can be any device suitable for delivery of the active agent at a controlled rate over a prolonged period of time. Thus, the device can take a wide variety of shapes and forms for administering the active agent at controlled rates to different areas of the body. The invention includes external and internal drug delivery devices such as transdermal patches, implants for releasing a therapeutically active agent in the body tissues, intravaginal rings, intracervical and intrauterine devices.

According to a preferred embodiment, the device is an implant for subcutaneous use, an intravaginal ring or an intrauterine device (IUD). According to the most preferred embodiments, the device is an implant for subcutaneous use or an intrauterine device.

Construction of the Core

The core of the device can consist of the active antiprogestin as such, e.g. in liquid or crystallized form, optionally in combination with other therapeutically active agents. Alternatively, the core can consist of the active agent or agents in a mixture with pharmaceutically acceptable excipients.

Preferably, the core is an elastomer matrix in which the drug is dispersed.

According to a particularly preferable embodiment, the core is made of a siloxane-based elastomer composition comprising at least one elastomer and possibly a non-crosslinked polymer. The elastomer composition comprises poly(alkylene oxide) groups where the poly(alkylene oxide) groups are present in the elastomer or polymer as alkoxy-terminated grafts of polysiloxane units, or as blocks, the said grafts or blocks being linked to the polysiloxane units by silicon-carbon bonds. The elastomer composition can also be a mixture of these forms.

Although the device, for example the implant, can be a plain core which consists of the elastomer matrix with the active agent(s) dispersed therein, the core is preferably encased in a membrane. The membrane is usually made of an elastomer.

According to a preferable embodiment, also the membrane is made of a siloxane-based elastomer composition comprising at least one elastomer and possibly a non-crosslinked polymer. The elastomer composition comprises poly(alkylene oxide) groups where the poly(alkylene oxide) groups are present in the elastomer or polymer as alkoxy-terminated grafts of polysiloxane units, or as blocks, the said grafts or blocks being linked to the polysiloxane twits by silicon-carbon bonds. The elastomer composition can also be a mixture of these forms.

According to another alternative, the matrix can be made of the afore mentioned elastomer composition while the membrane is made of normal PDMS (i.e. PDMS containing no poly(alkylene oxide)). Alternatively, the membrane can be made of the afore mentioned elastomer composition while the matrix is made of normal PDMS.

Manufacture of Implants

The implants according to this invention can be manufactured in accordance with standard techniques. The therapeutically active agent is mixed with the core matrix polymer such as PDMS or the components forming the elastomer composition as defined above, processed to the desired shape by molding, casting, extrusion, or other appropriate methods. The membrane layer can be applied onto the core according to known methods such as by mechanical stretching, swelling or dipping. Reference is made to the U.S. Pat. Nos. 3,832,252, 3,854,480 and 4,957,119. An especially suitable method for preparation of the implants is disclosed in the Finnish patent FI 97947. This patent discloses an extrusion technology where prefabricated rods containing the active ingredient are coated by an outer membrane. Each such rod is, for example, followed by another rod without any active ingredient. The formed string is cut at the rods that contain no active agent. In this way, no special sealing of the ends of the implant is necessary.

Intrauterine and Intracervical Devices

The intrauterine device can be made according to well known technology. A preferable intrauterine device (IUD) or intracervical device in common use is a T-shaped body made of plastic material such as polyethylene. The body consists of an elongate member (stem) having at one end a transverse member comprising two wings. The elongate member and the transverse member form a substantially T-shaped piece when the device is positioned in the uterus. The device has an attached thread long enough to protrude out of the cervical canal when the device is in position in the uterus. IUD:s releasing drugs have a drug reservoir adjusted around the elongate member. This drug reservoir is preferably a matrix which consists of the elastomer matrix with the active agent(s) dispersed therein. Preferably, the matrix is encased in a membrane. The membrane is usually made of an elastomer.

The drug reservoir adjusted around the stem of the T-shaped body can be manufactured as the implant as described above. Alternatively, the matrix can first be applied onto the stem after which the matrix is encased by a membrane.

The matrix and membrane of the drug reservoir on the IUD can be made of the same elastomers as the implants described above.

Drugs

As antiprogestinic compounds useful in this invention shall be understood compounds which compete at least to a certain extent with progesterone for its receptor and which therefore counteract the effect of progesterone at the receptor level. These compounds may be relatively pure antiprogestins, i.e. compounds without any significant other hormonal activities. These compounds may also exert a certain degree of other hormonal activities, for instance antiandrogenic and/or antiglucocorticoid activity. Suitable for the purpose of his invention are also compounds with antiprogestinic properties which in itself incorporate some degree of gestagenic activity and which are characterized by intermediate McPhail scores between those for anti-progestins without inherent gestagenic activity and progestins. It is also known that compounds with antiprogestinic properties may inherently possess some estrogenic activity.

The antiprogestinic compounds useful in this invention may be of steroidal or non-steroidal origin.

Examples of antiprogestins which can be employed in this invention are

11beta-[(4-(Dimethylamino)phenyl]-17beta-hydroxy-17alpha-(1-propinyl)-4,9-estradien-3-one (mifepristone)
11beta-[(4-(Dimethylamino)phenyl]-17beta-hydroxy-17alpha-(1-propinyl)-18-homoestra-4,9-dien-3-one
11beta-[(4-(Dimethylamino)phenyl]-17beta-hydroxy-17alpha-(1-propinyl)-17a-homoestra-4,9,16-trien-3-one and other corresponding compounds described in U.S. Pat. Nos. 4,386,085, 4,447,424, 4,519,946 and 4,634,695;

11beta-[(4-Dimethylamino)phenyl]-17alpha-hydroxy-17beta-(3-hydroxypropyl)-13α-methyl-estra-4,9-dien-3-one (onapristone)

and the other compounds described in U.S. Pat. No. 4,780,461 and EP 129499;

(Z)-11beta-[(4-dimethylamino)phenyl)]-17beta-hydroxy-17alpha-(3-hydroxy-1-propenyl)estra-4,9-dien-3-one (lilopristone)

and the other compounds described in U.S. Pat. No. 4,609,651;

11beta-(4-Acetylphenyl)-17beta-hydroxy-17alpha-(1-propinyl)estra-4,9-dien-3-one, (Z)-11beta-(4-acetylphenyl)-17beta-hydroxy-17alpha-(3-hydroxy-1-propenyl)estra-4,9-dien-3-one and the other compounds described in U.S. Pat. No. 5,089,635 and EP 190759;

11beta-(4-Methoxyphenyl)-17beta-hydroxy-17alpha-ethynyl-4,9-estradien-3-one and the other compounds described in Steroids 37 (1981), 361–382;

(Z)-11beta-[(4-Dimethylamino)phenyl)]-17beta-hydroxy-17alpha-(3-hydroxy-1-propenyl)estr-4-en-3-one and the other compounds described in EP 404283 and U.S. Pat. No. 5,728,689 as well as 11beta-aryl-estrene derivatives disclosed in e.g. U.S. Pat. Nos. 5,843,933 and 5,843,931

4-[17β-Methoxy-17α-(methoxymethyl)-3-oxoestra-4,9-dien-11β-yl]benzaldehyde-1-(E]-oxime,
4-[17β-Hydroxy-17α-(methoxymethyl)-3-oxoestra-4,9-dien-11β-yl]benzaldehyde-1-(E)-oxime, and the other compounds described in U.S. Pat. No. 5,693,628 and EP 648778;

4-[17β-Methoxy-17α-(methoxymethyl)-3-oxoestra-4,9-dien-11β-yl]benzaldehyde-1-(E)-[O-(ethylamino)carbonyl]oxime,
4-[17β-Methoxy-17α-(methoxymethyl)-3-oxoestra-4,9-dien-11β-yl]benzaldehyde-1-(E)-[O-(ethoxy)carbonyl]oxime and the other compounds described in U.S. Pat. No. 5,576,310 and EP 648779;

4-[17β-Methoxy-17α-(methoxymethyl)-3-oxoestra-1,9-dien-11β-yl]benzaldehyde-1-(E)-[O-(ethylthio)carbonyl]oxime,
4-[17β-Methoxy-17α-(ethoxymethyl)-3-oxoestra-4,9-dien-11β-yl]benzaldehyde-1-(E)-[O-(ethylthio)carbonyl]oxime,
4-[17β-Hydroxy-17α-(methoxymethyl)-3-oxoestra-4,9-dien-11β-yl]benzaldehyde-1-E)-[O-(n-propylthio)carbonyl]oxime and the other compounds described in DE 19809845 and WO 99/45023;

(Z)-6'-(4-cyanophenyl)-9,11α-dihydro-17beta-hydroxy-17α-[4-(1-oxo-3-methylbutoxy)-1-butenyl]4'H-naphtho[3',2',1';10,9,11]estr-4-en-3-one, (Z)6'-(4-cyanophenyl)-9,11α-dihydro-17beta-hydroxy-17α-[3-(1-oxo-3-methylbutoxy)-1-propenyl]4'H-naphtho[3',2',1';10,9,11]estra-4,15-dien-3-one, and the other compounds described in DE 196 52 408 and WO98/24803 as well as in DE 4434488, DE 4216003 and DE 4216004;

(Z)-6'-(4-cyanophenyl)-9,11α-dihydro-17beta-hydroxy-17α-(3-hydroxy-1-propenyl)-4'H-naphtho[3',2',1';10,9,11]estra-4,15-dien-3-one, (Z)-6'-(3-pyridinyl)-9,11α-dihydro-17beta-hydroxy-17α-(3-hydroxy-1-propenyl)-4'H-naphtho[3',2',1';10,9,11]estra-4,15-dien-3-one, 11βO-(4-acetylphenyl)-17β-hydroxy-17α-(1,1,2,2,2-pentafluoroethyl)estra-4,9-dien-3-one, 6'-(Acetyloxy)-9,11α-dihydro-17β-hydroxy-17α-(1,1,2,2,2-pentafluoroethyl)-4'H-naphth[3',2',1';10,9,11]estr-4-en-3-one, 9,11 α-Dihydro-17β-hydroxy-6'-(hydroxymethyl)-17α-(1,1,2,2,2-pentafluoroethyl)-4'H-naphth[3',2',1';10,9,11]estr-4-en-3-one and the other compounds described in WO 98/34947;

11beta-(4-Acetylphenyl)-19,24-dinor-17,23-epoxy-17alpha-chola-4,9,20-trien-3-one,
11beta-(4-Methoxyphenyl)-19,24-dinor-17,23-epoxy-17alpha-chola-4,9,20-trien-3-one, and the other compounds described in U.S. Pat. No. 5,292,878;

(Z)-11beta,19-[4-(3-Pyridinyl)-o-phenylene)-17beta-hydroxy-17α-[3-hydroxy-1-propenyl]-4-androsten-3-one,
(Z)-11beta,19-[4-(4-Cyanophenyl-o-phenylene)]-17beta-hydroxy-17α-[3-hydroxy-1-propenyl]-4-androsten-3-one and the other compounds described in WO 93/23020 and U.S. Pat. No. 5,439,913;

11beta-[4-(1-methylethenyl)phenyl]-17α-hydroxy-17beta-(3-hydroxypropyl)-13α-estra-4,9-dien-3-one,
11beta-[4-(3-Furanyl)phenyl]-17α-hydroxy-17beta-(3-hydroxypropyl)-13α-estra-4,9-dien-3-one and the other compounds described in EP 349481 and U.S. Pat. No. 5,446,036;

4',5'-Dihydro-11beta-[4-(dimethylamino)phenyl]-6beta-methylspiro[estra-4,9-dien-17beta,2'(3'H)-furan]-3-one,
4',5'-Dihydro-11beta-[4-(dimethylamino)phenyl]-7beta-methylspiro[estra-4,9-dien-17beta,2'(3'H)-furan]-3-one and the other compounds described in U.S. Pat. No. 4,921,845 and EP 321010;

4-beta,17α-Dimethyl-17beta-hydroxy-3-oxo-4α,5-epoxy-5α-androstan-2α-carbonitrile
7α-[9-(4,4,5,5,5-Pentafluoropentyl)sulfinyl]nonyl]estra-1,3,5(10)-trien-3,17beta-diol Additional examples of drugs are 11-beta-aryl-estradienes disclosed e.g. in U.S. Pat. Nos. 4,829,060, 4,814,327, and 5,089,488;

11beta-aryl-4,9-gonadiens and 11-beta-aryl-13-alkyl-4,9-gonadiens disclosed e.g. in U.S. Pat. Nos. 5,739,125; 5,407,928 and 5,273,971.

11beta-aryl-6-alkyl (or alkenyl or alkinyl) steroids disclosed e.g. in EP 289073; 10beta, 11beta-bridged steroids disclosed e.g. in U.S. Pat. No. 5,093,507;

11beta-aryl-14beta-steroids disclosed e.g. in U.S. Pat. No. 5,244,886 and EP 277676;

19,11beta-bridged steroids disclosed e.g. in U.S. Pat. Nos. 5,095,129, 5,446,178, 5,478,956, 5,232,915, EP 559690, and EP 283428;

As examples of non steroidal compounds can be mentioned 1-arylsulphonyl, arylcarbonyl and 1-arylphosphonyl-3-phenyl-1,4,5,6-tetrahydropyridazines such as
3-(4-chloro-3-trifluoromethylphenyl)-1-(4-iodobenzenesulphonyl)-1,4,5,6-tetrahydropyridazine;
(R,S) 3-(4-chloro-3-trifluoromethylphenyl)-1-(4-iodobenzenesulphonyl)-6-methyl-1,4,5,6-tetrahydropyridazine;
3-(3,4-dichlorophenyl)-1-(3,5-dichlorobenzoyl)-1,4,5,6-tetrahydropyridazine;
3-(3,4-dichlorophenyl)-1-(2,5-dichlorobenzenesulphonyl)-1,4,5,6-tetrahydropyridazine;

and the other compounds described in U.S. Pat. No. 5,684,151;

1-Arylsulphonyl, arylcarbonyl and arylthiocarbonyl pyridazino derivatives such as
7,8-Dibromo-3,4-diazo-1,2,3,10,10a-hexahydro-3-(4-iodobenzenesulphonyl)-phenanthrene,
7-Chloro-3,4-diazo-1,2,3,9,10,10a-hexahydro-3-(2,5-dichlorobenzenesulphonyl)-phenanthrene, and the other compounds described in U.S. Pat. No. 5,753,655;
non-steroidal compounds that are modulators (i.e. agonists and antagonists) of steroid receptors such as 1,2-dihydro-[1,2-g]quinoline derivatives
1,2-dihydro-chromeno-[3,4f]quinoline derivatives and the compounds described in U.S. Pat. Nos. 5,688,808, 5,693,646, 5,693,647, 5,696,127, 5,696,130 and 5,696,133.

The most preferred compounds are those explicitly mentioned by name above.

Typical diseases or conditions to be treated by the compounds having antiprogestinic properties:

The compounds of formula I in WO 98/34947 are competitive progesteron antagonists, which prevent progesteron from binding to its receptor. At the same instant other endocrinic side effects such as e.g. androgen, estrogen or antiglucocorticoidal activity are non-existent or minimal. The compounds can be used for contraception, for treating hormonal irregularities, to start the menstrual cycle and to start the labor. Further indications are hormone replacement therapy (WO-A 94/18983), treating of the pain connected to dysmenorrhoea, endometriosis (EP-A 0 266 303) as well as treating of myomas.

The compounds described in this invention are also suitable for treating hormone dependent carcinomas. Furthermore, combined with other active substances such as antiestrogens the compounds described in this invention can be used for treating hormone dependent tumors (EP-A 0 310 542) and for contraception (WO 96/19997). Without limiting the scope of this invention, antiestrogen can be e.g. tamoxifen, ICI 182.780, antiestrogens described in PCT/

EP97/04517 and aromatase inhibitors, such as fadrozol, formestan, letrozol, anastrozol or atamestan or any other therapeutically active substance with antiestrogenic properties.

Many antiprogestinic compounds are also useful for the prevention and or treatment of osteoporosis.

Antiprogestins combined with e.g: gonadotropin releasing hormone analog can be used for treating an ovarian estrogen dependent condition such as endometriosis, uterine leiomyomata, PMS (premenstrual syndrome) or DUB (dysfunctional uterine bleeding), a method without rapid loss of bone density as wit GnRH analogs alone (U.S. Pat. No. 5,681,817). Antiprogestins combined with progesterone synthesis inhibitors are suitable for treatment of endometriosis, dysmenorrhea and hormone dependent tumors (e.g. U.S. Pat. No. 5,795,881). Antiprogestins in combination with estrogens are useful in hormone replacement therapy in women.

Antiprogestins may also be used in combination with other hormones, progestins, mesoprogestins or other therapeutically active compounds such as flutamide, hydroxyflutamide, prostaglandins, glucocorticoids etc.

The required dose of the antiprogestinic compounds is disclosed in the art. The suitable dose range will vary with the particular condition to be treated, the severity of the condition, the duration of the treatment, the administration route and the specific compound being employed.

As examples can be mentioned:

compounds of U.S. Pat. No. 5,753,655 for contraception, menopause, endometriosis, breast cancer, cycle synchrony, pregnancy termination, labor induction or osteoporosis, most likely contraception, endometriosis and osteoporosis: 1–500 mg/kg, preferably 10–100 mg/kg/day mifepristone (0.05–10 mg/kg, pref. 0.5–5.0 mg/kg daily), compounds U.S. Pat. No. 5,516,769 for fertility control, without preventing ovulation: oral, depot, 0.01–1 mg, 0.05–0.5 mg compounds of U.S. Pat. No. 5,439,913 for contraception (by inhibiting the formation of endometrial glands and epithelium growth, the implantation of a fertilized egg in the uterus is rendered impossible, less than ovulation inhibiting and less than abortion inductive dose): 0.25–50 mg daily dose/implant vaginal ring.

The desired daily dosage of the drug in vivo for a defined condition to be treated, for a defined drug and administration route can be achieved with the device according to the invention particularly by varying the elastomer composition of the matrix or membrane or both so that it will contain a proper amount of poly(alkylene oxide) groups. An increasing concentration of such groups in the device will increase the drug permeation. In addition to the amount of poly (alkylene oxide) groups in the elastomer, other parameters such as the size and form of the device, the drug load, etc. will influence the daily dose released from said device. Some, but not undue, experimentation will be needed to find the most suitable parameters for each combination. The examples disclosed in the following will offer the necessary guidance for such experimentation.

The invention is described below in greater detail with the help of examples.

Experimental Section

Examples 1 to 10 describe the preparation of membranes made from different elastomer compositions.

Elastomer compositions of different types (A–J) were prepared. Of most composition types there were prepared different compositions which differed one from another with respect to the PEO amount. Elastomer membranes representing the different compositions were tested with respect to the permeation rates of various drugs.

Elastomer Compositions Prepared

In the elastomer compositions A–H described below, an addition reaction between vinyl groups and silyl hydride groups was used for the crosslinking, i.e. for producing a network structure. The hydride-functional siloxane polymer serving as the crosslinking agent contained at least two Si—H groups, which reacted with the carbon-carbon double bond of the polymer to be crosslinked. Membranes made from elastomer compositions I and J were prepared by using peroxide as the catalyst for crosslinkings in which case the vinyl or methyl groups reacted, forming carbon-carbon bonds. In all the composition types except composition types A, D, F and H, there was first prepared a basic polymer blend, in which case all of the vinyl-containing polymers and the fillers, or vinyl-containing polymers which contained a filler, were mixed together. The filler used was silica. Composition types A, D, F and H had only one vinyl-containing polymer each, and thus they themselves were basic polymers. The basic polymer blend was divided into portions I and II. The catalyst was added to portion I and the crosslinking agent and the inhibitor to portion II. Portions I and II were combined immediately before the crosslinking. The obtained blend was crosslinked at a temperature which was higher than the decomposition temperature of the inhibitor and at which the crosslinking reaction took place at the desired rate.

A blend can be made of the compositions also directly in one step, in which case the ingredients can be added in the following order: vinyl-containing polymers, inhibitor, catalyst and crosslinking agent.

The following table describes elastomer membranes of different composition types and their initial components.

TABLE 1

| Composition type | Polymers containing vinyl groups in the basic polymer blend | Crosslinking agent |
|---|---|---|
| A | α,ω-divinyl ether poly(ethylene oxide)-poly(dimethyl siloxane) multi-block copolymer (PEO-(PDMS-PEO)$_n$) | Hydride-functional siloxane |
| B | PEO-(PDMS-PEO)$_n$ and a siloxane polymer containing a filler | Hydride-functional siloxane |
| C | PEO-(PDMS-PEO)$_n$ separately or together with a siloxane polymer which does or does not contain a filler | α,ω-bis(dimethyl silyl hydride)-poly(dimethyl siloxane)-poly(ethylene oxide) multiblock copolymer (PDMS-(PEO-PDMS)$_n$) separately or together with a |

TABLE 1-continued

| Composition type | Polymers containing vinyl groups in the basic polymer blend | Crosslinking agent |
| --- | --- | --- |
| | | hydride-functional siloxane |
| D | α,ω-divinyl ether poly(ethylene oxide) (PEODIVI) | Hydride-functional siloxane |
| E | PEODIVI and a siloxane polymer which does or does not contain a filler | Hydride-functional siloxane |
| F | PEO-grafted dimethyl siloxane-methyl vinyl siloxane copolymer (PDMS-PEO graft copolymer) | Hydride-functional siloxane |
| G | PDMS-PEO graft copolymer and a siloxane polymer which does or does not contain a filler | Hydride-functional siloxane |
| H | α,ω-diallyl ether poly(ethylene oxide)-poly(dimethyl siloxane) multiblock copolymer (APEO-(PDMS-APEO)$_n$ | Hydride-functional siloxane |
| I | PEO-(PDMS-PEO)$_n$ and a siloxane polymer which does or does not contain a filler | Peroxide |
| J | PDMS-PEO graft copolymer separately or together with a siloxane polymer which does or does not contain a filler | Peroxide |

EXAMPLE 1

Elastomer Membrane Prepared from Composition Type A

Ingredients used for the preparation of the elastomer membrane:

α,ω-divinyl ether PEO-PDMS block copolymer where the amount of PEO was 27.0% by weight and the vinyl content was 0.186 mmol/g.

Platinum catalyst Silopren U Katalysatoren Pt-D (Bayer AG), which had a platinum-siloxane complex in a vinyl-containing siloxane matrix. The platinum content was 1% by weight and the vinyl content was 0.5 mmol/g.

Crosslinking agent α,ω-di(trimethyl silyl) dimethyl siloxane-hydromethyl siloxane (DMS-HMS) copolymer Silopren U Vernetzer 730 (Bayer AG) having a Si—H content of 7.1 mmol/g, a molar mass of 2800 g/mol and a DMS group to HMS group ratio of 1:1.

Inhibitor 1-ethynyl-1-cyclohexanol (ETCH, Aldrich) having a decomposition temperature of +40° C.

The PEO(-PDMS-PEO)$_n$ which was used as the initial substance was prepared as follows:

50 g of anhydrous α,ω-divinyl ether poly(ethylene oxide) (PEODIVI) having a molar mass of 268 g/mol was weighed into a three-necked flask. In addition, 129.87 g of α,ω-bis (dimethyl silyl hydride) poly(dimethyl siloxane) (PDMSDIH, M$_n$=717 g/mol) and 30% by weight of toluene dried by distillation were weighed into the same vessel. Since vinyl groups were present in excess (3 mol-%) in the reaction, in the final product vinyl groups were obtained at both ends, which was essential for the subsequent crosslinking. The reaction solution was stirred over a magnetic sing plate at 200 rpm, and dry oxygen was directed through the solution in order to prevent the deactivation of the catalyst. The reaction solution was heated to 50° C., whereafter the catalyst (Pt(0) divinyl-tetramethyl disiloxane complex) was added to the solution through the septum. The amount of platinum was 30 ppm, calculated from the amount of reactants. Thereafter the polymerization was monitored by means of IR until the reactions were complete (loss of the Si—H peak at 2130 cm$^1$), which took approximately 4 h. After the polymerization, the toluene was distilled off from the solution by raising the temperature to 65° C. An by lowering the pressure to 5 mbar for a period of 1 h.

In the preparation of the elastomer, two blends were first prepared, portions I and II. Portion I contained PEO-(PDMS-PEO)$_n$ and the platinum catalyst. Portion II contained PEO-(PDMS-PEO)$_n$, the crosslinking agent and the inhibitor. Portions I and II were combined by mixing immediately before the crosslinking.

The amounts of the ingredients in the composition example in the final blend to be crosslinked were as follows:

Basic polymer PEO-(PDMS-PEO)$_n$ 94.87% by weight

Platinum catalyst 0.1% by weight

Crosslinkng agent 5.00% by weight

Inhibitor 0.03% by weight

Portion I was prepared using a chamber mixer. 5.489 g of the basic polymer and 0.011 g of the platinum catalyst were weighed into the mixing chamber. The ingredients were agitated until the blend was homogeneous.

The crosslinking agent and the inhibitor were combined before being mixed with portion II. The mixture of the crosslinking agent and the inhibitor was prepared by weighing 0.059 g of ETCH and 9.941 g of Silopren U Vernetzer 730 into a glass vessel and by sting the mixture in a water bath of +37° C. until ETCH had dissolved completely in the crosslinking agent. The amount of inhibitor in the mixture was 0.59% by weight.

Portion II was prepared using a chamber mixer. The mantle of the chamber mixer was cooled by water circulation to a point below room temperature, whereupon the temperature increase due to friction did not raise the temperature to the decomposition temperature of the inhibitor. 4.947 g of PEO-PDMS block copolymer and 0.553 g of the mixture of the crosslinking agent and the inhibitor were weighed into the mixing chamber. The ingredients were agitated until the blend was homogeneous.

Portions I and II were combined immediately before the crosslinking, by adding 5 grams of portion I and 5 grams of portion II into the mixing chamber of the chamber mixer. The ingredients were agitated until the blend was homogeneous. The blend was recovered and was drawn into vacuum to remove air bubbles. Four batches of 2 g of the blend were weighed and crosslinked successively in a hot-press.

The weighed blend was placed between two FEP release membranes in the center of a round metal form having a thickness of 0.4 mm and an inner diameter of 8 cm. The blend, together with the forms and the FEP membranes, was placed between the compression surfaces of the hot-press, which surfaces had been heated in advance to +115° C. The surfaces were pressed together and were kept pressed at a pressure of 200 bar for 5 minutes. The pressure was released and the membrane was allowed to set at room temperature for 24 hours. Round test pieces having a diameter of 22 mm were cut out from the membranes by means of a puncher.

EXAMPLE 2

Elastomer Membrane Prepared from Composition Type B

Ingredients used for the preparation of the elastomer membrane:

The PEO(-PDMS-PEO)$_n$ was the same as in Example 1, except that the amount of PEO had been increased to 28.0% by weight and the vinyl content to 0.24 mmol/g by increasing the proportion of PEODIVI in the synthesis of the block copolymer.

The catalyst, the crosslinking agent and the inhibitor were the same as in Example 1.

The siloxane polymer which contained filler was a dimethyl siloxane-vinyl methyl siloxane (DMS-VMS) copolymer containing a silica filler and having a molar mass of $M_n$=400,000 g/mol. The vinyl content of the blend was 0.011 mmol/g. There was 36% by weight of silica mixed in the polymer, and the silica was surface-treated with α,ω-bis(dimethyl hydroxysilyl) poly(dimethyl siloxane) (M=520 g/mol), which was present in an amount of 12% by weight in the blend.

The amounts of ingredients in the composition example were as follows:

PEO(-PDMS-PEO)$_n$ 32.8% by weight

DMS-VMS copolymer containing a silica filler, 60.9% by weight

Platinum catalyst 0.1% by weight

Crosslinkig agent 6.19% by weight

Inhibitor 0.03% by weight

First the basic polymer blend was prepared in a chamber mixer. 4.2 grams of the PEO(-PDMS-PEO)$_n$ block copolymer and 7.8 grams of the DMS-VMS copolymer containing a silica filler were weighed into the mixing chamber. The ingredients were agitated until the blend was homogeneous.

Portion I was prepared as in Example 1.

The combining of the crosslinkig agent and the inhibitor was done, as in Example 1, before mixing with portion II, except that ETCH was weighed in an amount of 0.048 g and Silopren U Vernetzer 730 in an amount of 9.952 g. The amount of inhibitor in the blend was 0.48% by weight.

Portion II was prepared as in Example 1, except that the basic polymer blend was weighed in an amount of 4.816 grams and the mixture of the crosslinkig agent and the inhibitor in an amount of 0.684 grams.

Portions I and II were combined as in Example 1. Four batches of 2.1 g of the blend were weighed and were crosslinked successively in a hot-press, as in Example 1.

EXAMPLE 3

Elastomer Membrane Prepared from Composition Type C

Ingredients used for the preparation of the elastomer membrane:

The PEO(-PDMS-PEO)$_n$ was the same as in Example 2. The catalyst and the inhibitor were the same as in Examples 1 and 2.

The dimethyl siloxane-vinyl methyl siloxane (DMS-VMS) copolymer containing a silica filler was the same as in Example 2.

The crosslinking agent used was a PDMS-(-PEO-PDMS)$_n$ copolymer having a Si—H content of 0.26 mmol/g, and the amount of PEO in it was 23.6% by weight.

The said crosslinking agent was prepared as follows:

40 g of an anhydrous α,ω-divinyl ether poly(ethylene oxide) (PEODIVI) having a molar mass of 246.3 g/mol was weighed into a three-necked flask. In addition, 129.4 g of α,ω-bis(dimethyl silyl hydride) poly(dimethyl siloxane) PDMSDIH, $M_n$=717 g/mol) and 30% by weight of toluene dried by distillation were weighed into the same vessel. Since dimethyl silyl hydride groups were present in excess (10 mol-%) in the reaction, dimethyl silyl hydride groups were obtained at both ends in the final product. The reaction solution was stirred over a magnetic sting plate at 200 rpm, and dry oxygen was directed through the solution to prevent the deactivation of the catalyst. The reaction solution was heated to 50° C., whereafter the catalyst (Pt(0) divinyl-tetramethyl siloxane complex) was added to the solution through the septum. The amount of platinum was 30 ppm, calculated from the amount of the reactants. Thereafter the polymerization was monitored by means of IR until the reactions were complete (loss of the vinyl peak at 1600 cm$^1$), which took approximately 4 h. After the polymerization, the toluene was removed from the solution by distillation by raising the temperature to 65° C. and by lowering the pressure to 5 mbar for a period of 1 h.

The amounts of the ingredients in the composition example were as follows:

PEO(-PDMS-PEO)$_n$ 1.10% by weight

DMS-VMS containing a silica filler, 85.50% by weight

Platinum catalyst 0.10% by weight

Crosslinkig agent α,ω-bis-(dimethyl silyl hydride) PEO-PDMS 13.27% by weight

Inhibitor 0.03% by weight

First the basic polymer blend was prepared in a chamber mixer. 0.15 grams of the α,ω-divinyl ether PEO-PDMS block copolymer and 11.85 grams of the DMS-VMS copolymer containing a silica filler were weighed into the mixing chamber. The ingredients were agitated until the blend was homogeneous.

Portion I was prepared as in Example 1. The combining of the crosslinking agent and the inhibitor was done, as in Example 1, before mixing with portion II, except that ETCH was weighed in an amount of 0.022 g and PDMS-(PEO-PDMS)$_n$ block copolymer in an amount of 9.978 g instead of Vernetzer 730. The amount of inhibitor in the blend was 0.22% by weight.

Portion II was prepared as in Example 1, except that the basic polymer blend was weighed in an amount of 4.04 grams and the mixture of the crosslinking agent and the inhibitor in an amount of 1.46 grams.

Portions I and II were combined as in Example 1. Four batches of 2.1 g of the blend were weighed and were successively crosslinked in a hot-press, as in Example 1.

EXAMPLE 4

Elastomer Membrane Prepared from Composition Type D

Ingredients used for the preparation of the elastomer membrane:

α,ω-divinyl ether poly(ethylene oxide) (PEODIVI) (polyethylene glycol divinyl ether, Aldrich, $M_n$=240 g/mol). The vinyl amount obtained by titration was 7.4 mmol/g.

Catalyst Gelest SIP 6831.0, platinum-siloxane complex in xylene, platinum content 2.25% by weight.

The crosslinking agent and the inhibitor were the same as in Example 1.

The amounts of the ingredients in the composition example were as follows:

PEODIVI 52.231% by weight
Platinum catalyst 0.045% by weight
Crosslinking agent 47.694% by weight
Inhibitor 0.030% by weight First a mixture of the crosslinking agent and the inhibitor was prepared as in Example 1, except that the inhibitor was weighed in an amount of 0.0063 grams and the crosslinking agent in an amount of 9.9937 grams. The amount of inhibitor in the mixture was 0.063% by weight.

5.2231 grams of PEODIVI and 0.0045 grams of the platinum catalyst were mixed together in a glass vessel. 4.772 grams of the mixture of the crosslinking agent and the inhibitor was mixed into it.

Eight batches of 0.8 g of the blend were weighed into flat-bottomed aluminum forms having a diameter of 5 cm and having a FEP membrane on the bottom. The forms were placed under a 100 mbar vacuum at +115° C. for a period of 15 minutes. Test pieces were cut out from the elastomer obtained.

EXAMPLE 5
Elastomer Membrane Prepared from Composition Type E

Ingredients used for the preparation of the elastomer membrane:

PEODIVI, the same as in Example 4.
DMS-VMS copolymer, the same as in Example 2.

The catalyst, the crosslinking agent and the inhibitor were the same as in Example 1.

The amounts of the ingredients in the composition example were as follows:

PEODIVI 11.37% by weight
DMS-VMS copolymer 64.46% by weight
Platinum catalyst 0.1% by weight
Crosslinking agent 24.03% by weight
Inhibitor 0.03% by weight First, a mixture of the crosslinking agent and the inhibitor was prepared, as in Example 1, except that the inhibitor was weighed in an amount of 0.0125 grams and the crosslinking agent in an amount of 9.9875 grams. The amount of inhibitor in the mixture was 0.125% by weight.

1.138 grams of PEODIVI and 6.446 grams of DMS-VMS copolymer were mixed together in a chamber mixer. 0.01 grams of platinum catalyst was added, and the blend was agitated until homogeneous. 2.406 grams of the mixture of the crosslinking agent and the inhibitor was added and the blend was agitated until homogeneous.

Four batches of 2.1 g of the blend were weighed and were successively crosslinked in a hot-press, as in Example 1.

EXAMPLE 6
Elastomer Membrane Prepared from Composition Type F

Ingredients used for the preparation of the elastomer membrane:

PDMS-PEO graft copolymer having a vinyl concentration of 0.0743 mmol/g and a PEO content of 1.28% by weight.

The catalyst, the crosslinking agent and the inhibitor were the same as in composition A.

The PDMS-PEO graft copolymer used was prepared as follows:

600 g of octamethyl cyclotetrasiloxane ($D_4$), 9.28 g of poly(dimethyl siloxane)poly(ethylene oxide) graft copolymer (Gelest, DBE-821, containing 80% by weight PEO), 6.18 g of dimethyl vinyl silyl end-blocked PDMS (end-blocker, Bayer Silopren U2), and 3.1 g of tetramethyl tetravinyl cyclotetrasiloxane were weighed. The reactor was nitrogenated, the weighed chemicals were poured in, and stirring was started. The inside temperature of the reactor was raised to 135° C., and the catalyst (potassium siloxanolate, 0.9 ml, 20 ppm $K^+$) was added to the reaction solution. The viscosity of the reaction solution began to increase vigorously, and at 1 h from the adding of the catalyst it was possible to deactivate the catalyst by increasing the reactor pressure to 2 bar for a period of 15 minutes by means of carbon dioxide. Thereafter the light cyclic compounds (13% by weight) were removed from the reaction solution by distillation (10 mbar, 30 min 135° C.). Product $M_n$=190,000 g/mol.

The amounts of the ingredients in the composition example were as follows:

Basic polymer PDMS-PEO graft copolymer 96.10% by weight
Platinum catalyst 0.5% by weight
Crosslinking agent 3.06% by weight
Inhibitor 0.34% by weight The combining of the crosslinking agent and the inhibitor was done as in Example 1, except that ETCH was weighed in an amount of 1.0 g and Silopren U Vernetzer 730 in an amount of 9.0 g. The amount of inhibitor in the mixture was 10% by weight.

9.61 grams of the PDMS-PEO graft copolymer and 0.05 grams of the platinum catalyst were mixed together. 0.34 grams of the mixture of the crosslinking agent and the inhibitor was added and the blend was stirred until homogeneous.

Four batches of 2.1 g of the blend were weighed and were successively crosslinked in a hot-press, as in Example 1.

EXAMPLE 7
Elastomer Membrane Prepared from Composition Type G

Ingredients used for the preparation of the elastomer membrane:

The PDMS-PEO graft copolymer was the same as in Example 6.

The DMS-VMS copolymer was the same as in Example 2.

The catalyst, the crosslinking agent and the inhibitor were the same as in Example 1.

The amounts of the ingredients in the composition example were as follows:

PDMS-PEO graft copolymer 26.75% by weight
DMS-VMS copolymer 72.31% by weight
Platinum catalyst 0.10% by weight
Crosslinking agent 0.81% by weight
Inhibitor 0.03% by weight The combining of the crosslinking agent and the inhibitor was done as in Example 1, except that ETCH was weighed in an amount of 0.36 g and Silopren U Vernetzer 730 in an amount of 9.64 g. The amount of inhibitor in the mixture was 3.6% by weight.

2.675 grams of the PDMS-PEO graft copolymer and 7.231 grams of the DMS-VMS copolymer containing a filler were mixed together. 0.01 grams of the platinum catalyst was added and the blend was stirred until homogeneous. 0.084 grams of the mixture of the crosslinking agent and the inhibitor was added and the blend was stirred until homogeneous.

Four batches of 2.1 g of the blend were weighed and were successively crosslinked in a hot-press, as in Example 1.

EXAMPLE 8
Elastomer Membrane Prepared from Composition Type H

Ingredients used for the preparation of the elastomer membrane;

APEO-(-PDMS-APEO)$_n$, where the amount of PEO was 10.3% by weight and the vinyl content 0.063 mmol/g.

The catalyst was the same as in Example 4.

The inhibitor was the same as in Example 1.

The crosslinking agent was a DMS-HMS copolymer which contained 22.5% by weight methyl hydride siloxane groups (Gelest).

The APEO-(PDMS-APEO)$_n$ used was prepared as follows:

Anhydrous α,ω-diallyl poly(ethylene oxide) (PEODIAL) which had a molar mass of 520 g/mol and which was prepared by adapting the procedure disclosed in the publication Mei-Hui, Yang, Laing-Jong, Li, and Tsang-Feng, Ho, Synthesis and Characterization of polymethylsiloxane/poly (ethylene glycol)monomethyl ether copolymers, J. Ch. Colloid & Interface Soc. 3(17), 1994, 19–28 and α,ω-bis (dimethyl silyl hydride) poly(dimethyl siloxane) (PDMSDIH, M$_n$=6000 g/mol) were weighed into a three-necked flask. The mass of the PEODIAL was 1.38 g (M$_n$=520 g/mol, 5.28 mmol of allyl groups) and the mass of PDMSDIH was 12 g (4.8 mmol of hydride groups), the amount of allyl groups being 10% greater than that of hydride groups. Thus an α,ω-diallyl-end-blocked final product was ensured.

In addition, toluene was weighed into the reaction vessel in an amount of 45% by weight (7.2 g). The reaction mixture was stirred over a magnetic stirring plate at 200 rpm, and dry oxygen was bubbled through the mixture in order to prevent the deactivation of the catalyst. The temperature of the reaction mixture was raised to 60° C. Thereafter the catalyst (Pt(0) divinyl tetramethyl disiloxane complex) was added to the reaction solution through the septum, cautiously one drop at the time. The amount of platinum was 50 ppm, calculated from the reactants. The polymerization was allowed to proceed for approximately 6 h, whereafter the completion of the polymerization was confirmed by IR (loss of the Si—H peak at 2130 cm$^{-1}$). For the removal of the toluene by distillation, the temperature was raised to 65° C. and the pressure was lowered to 5 mbar for a period of 30 min.

The amounts of the ingredients of the composition example were as follows:

APEO-(-PMDS-APEO)$_n$ 94.68% by weight

Platinum catalyst 0.5% by weight

Crosslinking agent 4.7% by weight

Inhibitor 0.12% by weight 3.0 grams of the APEO-(-PMDS-APEO)$_n$, 0.018 grams of the catalyst, 0.0038 g of the inhibitor, and 0.1489 g of the crosslinking agent were mixed together. The air bubbles were removed from the mixture, and the mixture was crosslinked in a hot-press at 110° C. for 15 minutes and was cured at 110° C. for 15 minutes.

EXAMPLE 9
Elastomer Membrane Prepared from Composition Type I

Ingredients used for the elastomer membrane:

PEO-(PDMS-PEO)$_n$, where the amount of PEO was 5.0% by weight and the vinyl content was 0.04 mmol/g.

The DMS-VMS copolymer containing a silica filler was the same as in Example 2.

Dichlorobenzoyl peroxide (Perkadox PD50 S).

The PEO-(PDMS-PEO)$_n$ used was prepared as follows:

0.528 g of anhydrous α,ω-divinyl ether poly(ethylene oxide) (PEODIVI) having a molar mass of 240 g/mol was weighed into a three-necked flask. 10 g of α,ω-bis(dimethyl silyl hydride)poly(dimethyl silyl siloxane) (PDMSDIH) having a molar mass of 6000 g/mol was weighed into the same vessel. The PDMSDIH contained hydride groups in an amount of 0.04% by weight, and thus the amount of hydride groups in 10 grams was 4 mmol and the amount of PEO-DIVI vinyl groups was 4.4 mmol. Since the vinyl groups were present in excess (10 mol-%) in the reaction, vinyl groups were obtained at both ends of the final product, a fact essential for the subsequent crosslinking. In addition, to facilitate mixing and to prevent the reaction from occurring too vigorously, toluene dried by distillation was added to the reaction mixture so that the proportion of toluene was 30% by weight (4.5 g). The reaction solution was stirred over a magnetic stirring plate at 200 rpm, and dry oxygen was directed through the solution; this prevented the catalyst from converting to metallic form and thus prevented the deactivation of the catalyst. The reaction solution was heated to 50° C., whereafter the catalyst (Pt(0) divinyl tetramethyl disiloxane complex) was added to the mixture through the septum. The amount of platinum was 50 ppm, calculated from the amount of the reactants. The catalyst was added dropwise, whereby hot spots in the reactor were avoided. After the adding of the catalyst the reaction was allowed to proceed for 2 h. Thereafter the completion of the reaction was confirmed by IR (loss of the Si—H peak at 2130 cm$^{-1}$). After the polymerization the reaction mixture was heated to 65° C. and the toluene was removed by vacuum distillation (5 mbar) in the course of 30 minutes.

The amounts of ingredients in the composition example were as follows:

PEO-(PDMS-PEO)$_n$, 4.9% by weight silica-filled DMS-VMS copolymer, 93.9% by weight dichlorobenzoyl peroxide (Perkadox PD50 S), 1.2% by weight.

0.5 g of PEO-(PDMS-PEO)$_n$ and 9.5 g of a DMS-VMS copolymer containing a filler were mixed together. 0.12 g of the peroxide catalyst was mixed with the homogeneous blend, and the blend was hardened at a temperature of +115° C. and a pressure of 200 bar for 5 minutes and was cured at +150° C. for 2 hours.

EXAMPLE 10
Elastomer Membrane Prepared from Composition Type J

Ingredients used for the preparation of the elastomer:

PDMS-PEO graft copolymer the same as in Example 6

Dichlorobenzoyl peroxide Perkadox PD50 S

The amounts of the ingredients in the composition example were as follows:

PDMS-PEO graft copolymer 98.8% by weight

Dichlorobenzoyl peroxide Perkadox PD50 S 1.2% by weight 10 grams of the PDMS-PEO graft copolymer and 0.12 grams of Perkadox PD50 S were mixed together. The blend was hardened at a temperature of +115° C. and a pressure of 200 bar for 5 minutes and was cured at +150° C. for 2 hours.

The following Examples 11 to 15 demonstrate different devices for the release of antiprogestins. These examples show modified drug release from different elastomer matrixes and membranes. Elastomers of different composition types (A–C, E and G) and poly-(dimethylsiloxane-co-vinylmethylsiloxane) with or without silica filler were used in these preparations.

EXAMPLE 11

The implants described in this Example as well as in Example 13 consist of three parts: a core with the drug in a polymer matrix, a membrane covering the core and silicone adhesive end-caps.

a) Antiprogestin Containing Implant Based on the New Elastomer Composition

This implant contains two different elastomer composition types (B and E) and and poly(dimethylsiloxane-co-vinylmethylsiloxane).

Membrane 26 parts of elastomer composition type B, 71 parts of silica-filled poly(dimethylsiloxane-co-vinylmethylsiloxane), 10 ppm Pt-catalyst (of the reaction species), 0.03 parts of inhibitor (ethynyl cyclohexanol) and approx. 2 parts of poly(hydrogenmethylsiloxane-co-dimethylsiloxane) crosslinker were mixed in a 2-roll mill. The mixture was extruded to a tube-like form with a wall thickness of 0.2 mm and cured by heat.

Core 29 parts of elastomer composition type E, 29 parts of poly(dimethylsiloxane-co-vinylmethylsiloxane), 10 ppm Pt-catalyst (of the reaction species), 0.02 parts of inhibitor (ethynyl cyclohexanol) and approx. 2.4 parts of poly (hydrogenmethylsiloxane-co-dimethylsiloxane) crosslinker were mixed in a 2-roll mill and 39 parts of the antiprogestin denoted as compound 4 in Table 2 below were added. The mixture was casted to a PTFE-coated stainless steel mold, which was heated at +150° C. for 30 minutes. The cores were removed, cooled and cut to desired length (5 mm).

Preparation of the Implant

The membrane tubes (length 50 mm) were swelled with cyclohexane and the cores were inserted. Cyclohexane was allowed to evaporate and ends were closed with a silicone adhesive. After 24 hours the ends were cut to give 2 mm end-caps.

b) Antiprogestin Containing Implant Based on the New Elastomer Composition

This implant was the same as that described in a) above except that the length of the core was 13 mm.

c) Antiprogestin Containing Implant Based on the Use of PDMS

Membrane

The silicone membrane corresponds to a commercial silica-filled poly(dimethylsiloxane) membrane and it was prepared as follows:

99 parts of silica-filled poly(dimethylsiloxane-co-vinylmethylsiloxane), 10 ppm Pt-catalyst (of the reaction species) and 0.03 parts of inhibitor (ethynyl cyclohexanol) and approx. 0.6 parts of poly-(hydrogenmethylsiloxane-co-dimethylsiloxane) crosslinker were mixed in a 2-roll mill. The mixture was extruded to a tube-like form with a wall thickness of 0.2 mm and cued in a shockoven. The tube shaped membrane cut to 50 mm pieces.

Core 59.3 parts of commercial poly-(dimethylsiloxane-co-vinylmethylsiloxane), 0.4 parts of poly-(hydrogenmethylsiloxane-co-dimethylsiloxane) crosslinker, 0.02 parts of ethynyl cyclohexanol inhibitor and 10 ppm Pt-catalyst (of the reaction species) in vinyl-methyl-siloxane were mixed in a two-chamber mixer. 40 parts of the antiprogestin denoted as compound 4 in Table 2 below were added and the mixture was mixed in a two-chamber mixer. The mixture was casted to a PTFE-coated stainless steel mold, which was heated at +150° C. for 30 minutes. The cores were removed, cooled and cut to desired length (5 mm).

Preparation of the Implant

The membrane tubes (length 50 mm) were swelled with cyclohexane and the cores were inserted. Cyclohexane was allowed to evaporate and ends were closed with a silicone adhesive. After 24 hours the ends were cut to give 2 mm end-caps.

EXAMPLE 12

The intrauterine device (IUD) described in this Example and in Examples 14 and 15 consists of three parts: a core with the drug in a polymer matrix, a membrane covering the core and a T-shaped body of polyethylene onto which the core surrounded by the membrane is applied.

a) Antiprogestin Containing IUD Based on the New Elastomer Composition

The IUD contains two different elastomer composition types (B, E) and poly-(dimethylsiloxane-co-vinylmethylsiloxane).

Membrane

The membrane was the same as in Example 11a.

Core 29 parts of elastomer composition type E, 29 parts of poly(dimethylsiloxane-co-vinylmethylsiloxane). 10 ppm Pt-catalyst (of the reaction species), approx. 0.02 parts of inhibitor (ethynyl cyclohexanol) and approx. 2.4 parts of poly-(hydrogenmethylsiloxane-co-dimethylsiloxane) crosslinker were mixed in a 2-roll mill and 39 parts of the antiprogestin denoted as compound 4 in Table 2 below were added. The mixture was extruded to a tube-like form with a wall thickness of 0.8 mm and cured by heat. The cores were cooled and cut into desired length (19 mm).

Preparation of the IUD

The membrane tubes (length 50 mm) and the cores were swelled with cyclohexane and applied onto the polyethylene T-shaped body of the device. Cyclohexane was allowed to evaporate.

b) Antiprogestin Containing IUD Based on the Use of PDMS

Membrane

The membrane was the same as described in Example 11c) above.

Core 100 parts of commercial poly-(dimethylsiloxane-co-vinylmethylsiloxane), 0.4 parts of poly-(hydrogenmethylsiloxane-co-dimethylsiloxane) crosslinker, 0.02 parts of ethynyl cyclohexanol inhibitor and 0.06 parts of platinum catalyst in vinyl-methylsiloxane were mixed in a two-chamber mixer. 67 parts of the antiprogestin denoted as compound 4 in Table 2 below were added and the mixture was mixed in a two-chamber mixer. The mixture was casted to a PTFE-coated stainless steel mold, which was heated at +115° C. for 30 minutes. The cores were removed, cooled and cut to desired length (19 mm).

IUD

The membrane tubes (length 50 mm) and the cores were swelled with cyclohexane and applied onto the polyethylene T-shaped body of the device. Cyclohexane was allowed to evaporate.

EXAMPLE 13 a) Antiprogestin Containing Implant Based on the New Elastomer Composition

This implant contains two different elastomer composition types (B and E) and and poly(dimethylsiloxane-co-vinylmethylsiloxane).

Membrane

The membrane was the same as described in Example 11a).

Core 50 parts of elastomer composition type E, 50 parts of poly-(dimethylsiloxane-co-vinylmethylsiloxane), 10 ppm Pt-catalyst (of the reaction species), 0.02 parts of inhibitor (ethynyl cyclohexanol) and approx. 2.4 parts of poly (hydrogenmethylsiloxane-co-dimethylsiloxane) crosslinker were mixed in a 2-roll mill. 67 parts of the antiprogestin denoted as compound 1 in Table 2 below were added. The mixture was casted to a PTFE-coated stainless steel mold, which was heated at +115° C. for 30 minutes. The cores were removed, cooled and cut to desired length (15 mm).

Preparation of the Implant

The membrane tubes (length 50 mm) were swelled with cyclohexane and the cores were inserted. Cyclohexane was allowed to evaporate and ends were closed with a silicone adhesive. After 24 hours the ends were cut to give 2 mm end-caps.

b) Antiprogestin Containing Implant Based on the Use of PDMS

Membrane

The membrane was the same as in Example 11c).

Core 100 parts of commercial poly-(dimethylsiloxane-co-vinylmethylsiloxane), 0.4 parts of poly-(hydrogenmethylsiloxane-co-dimethylsiloxane) crosslinker, 0.02 parts of ethynyl cyclohexanol inhibitor and 10 ppm Pt-catalyst (of the reaction species) in vinyl-methyl-siloxane were mixed in a two-chamber mixer. 67 parts of the antiprogestin denoted as compound 1 in Table 2 below were added and the mixture was mixed in a two-chamber mixer. The mixture was casted to a PTFE-coated stainless steel mold, which was heated at +115° C. for 30 minutes. The cores were removed, cooled and cut to desired length (15 mm).

Preparation of the Implant

The membrane tubes (length 50 mm) were swelled with cyclohexane and the cores were inserted. Cyclohexane was allowed to evaporate and ends were closed with a silicone adhesive. After 24 hours the ends were cut to give 2 mm end-caps.

EXAMPLE 14 a) Antiprogestin Containing IUD Based on the New Elastomer Composition

The IUD contains two different elastomer composition types (B, E) and poly(dimethylsiloxane-co-vinylmethylsiloxane).

Membrane

The membrane was the same as in Examples 11a) and 12a).

Core 50 parts of elastomer composition type E, 50 parts of poly(dimethylsiloxane-co-vinylmethylsiloxane), 10 ppm Pt-catalyst (of the reaction species), approx. 0.02 parts of inhibitor (ethynyl cyclohexanol) and approx 2.4 parts of poly(hydrogenmethylsiloxane-co-dimethylsiloxane) crosslinker were mixed in a 2-roll mill, and 67 parts of the antiprogestin denoted as compound 1 in Table 2 below were added. The mixture was extruded to a tube-like form with a wall thickness of 0.8 mm and cured by heat. The cores were cooled and cut into desired length (19 mm).

Preparation of the IUD

The membrane tubes (length 50 mm) and the cores were swelled with cyclohexane and applied onto the polyethylene T-shaped body of the device. Cyclohexane was allowed to evaporate.

b) Antiprogestin Containing IUD Based on the Use of PDMS

Membrane

The membrane was the same as described in Example 11c) above.

Core 100 parts of commercial poly-(dimethylsiloxane-co-vinylmethylsiloxane), 0.4 parts of poly-(hydrogenmethylsiloxane-co-dimethylsiloxane) crosslinker, 0.02 parts of ethynyl cyclohexanol inhibitor and 0.06 parts of platinum catalyst in vinyl-methylsiloxane were mixed in a two-chamber mixer. 67 parts of the antiprogestin denoted as compound 1 in Table 2 below were added and the mixture was mixed in a two-chamber mixer. The mixture was casted to a PTFE-coated stainless steel mold, which was heated at +115° C. for 30 minutes. The cores were removed, cooled and cut to desired length (19 mm).

IUD

The membrane tubes (length 50 mm) and the cores were swelled with cyclohexane and applied onto the polyethylene T-shaped body of the device. Cyclohexane was allowed to evaporate.

EXAMPLE 15 a) Antiprogestin Containing IUD Based on the New Elastomer Composition

The IUD is the same as that described in Example 14a) except that the antiprogestine is compound 2 in Table 2 below and the length of the core 15 mm.

b) Antiprogestin Containing IUD Based on the Use of PDMS

The IUD is the same as that described in Example 14b) except that the antiprogestine is compound 2 in Table 2 below and the length of the core 15 mm.

Permeation Tests Using Membranes of the New Elastomer Composition

Various compositions, in which the amount of PEO groups varied, were prepared of the above-mentioned composition types A–J. Composition types A–B were tested for the permeation rates of certain antiprogestins.

The assay apparatus described in the publication Yie W. Chien, Transdermal Controlled Systemic Medications, Marcel Dekker Inc., New York and Basel 1987, page 173, was used in the tests.

The drug fluxes (permeations) through membranes were measured with a two-compartment diffusion cell at 37° C. (Side-Bi-Side™ diffusion cell, Crown Glass Company). The apparatus consisted of two concentric cells (donor and receptor compartments) that were separated by the elastomer membrane to be investigated. The donor and receptor compartments were both jacketed and thermostated by an external circulating bath and each compartment had a magnetic stirrer. A drug solution and solvent (without drug) was added into the donor and the receptor compartments. At each predetermined time interval, samples were withdrawn from the receptor compartment and replaced with the same volume of solvent. The amount of the drug that permeated through the membrane was measured by HPLC. In all measurements, the thickness (0.4 mm) of the membrane and the surface area of the membranes were constant.

In the tests described below, the permeation rates of two different drugs through a 0.4-mm-thick elastomer membrane were measured by using the assay apparatus described above. The tables below show the effect of the concentration of PEO groups (% by weight of the said compositions) on the permeation rates of the different drugs for elastomers prepared from different composition types. The tables show the relative permeation as compared with a commercial crosslinked dimethyl siloxane-vinyl methyl siloxane elastomer ($M_n$ approximately 400,000 g/mol) containing a silica filler.

The compounds listed in Table 2 were subjected to this permeation test.

TABLE 2

Antiprogestins subjected to permeation tests:

| compound no | chemical name |
|---|---|
| 1 | 4-[17β-methoxy-17α-(methoxymethyl)-3-oxoestra-4,9-dien-11β-yl]benzaldehyde-1-(E)-oxime |
| 2 | 4-[17β-Methoxy-17α-(methoxymethyl)-3-oxoestra-4,9-dien-11β-yl]benzaldehyde-1-[O-(ethylamino)carbonyl]oxime |
| 3 | 11β-[17β-Methoxy-17α-(methoxymethyl)-3-oxoestra-4,9-diene-11β-yl]benzaldehyde-1(E)-[O-(ethylthio)carbonyl)-oxime] |
| 4 | 11β-(4-Acetylphenyl)-17β-hydroxy-17α-(1,1,2,2,2-pentafluoroethyl)estra-4,9-dien-3-one |
| 5 | Estr-4-en-3-one, 11-[4-(dimethylamino)phenyl]-17-hydroxy-17-(3-hydroxy-1-propenyl)-,[11.beta,17.beta.,17(Z)]-(9CI) |
| 6 | (Z)-6'-(4-Cyanophenyl)-17-β-hydroxy-17-α-(3-isovaleryloxy-1-propenyl))-9,11-α-diydro-4'H-naphth [3',2',1':10,9,11]estr-4-en-3-one |

Results of the Permeation Tests

Compound 1

| Composition type | PEO concentration % by weight | Relative permeation |
|---|---|---|
| reference | 0 | 1 |
| A | 4.7 | 3.5 |
| A | 5.1 | 5.3 |

Compound 2

| Composition type | PEO concentration % by weight | Relative permeation |
|---|---|---|
| reference | 0 | 1 |
| A | 4.7 | 4.1 |
| A | 5.1 | 7.6 |
| B | 3.1 | 3.7 |
| B | 4.1 | 4.1 |
| B | 5.0 | 5.8 |
| B | 7.5 | 11.5 |
| B | 9.8 | 17.3 |

Compound 3

| Composition type | PEO concentration % by weight | Relative permeation |
|---|---|---|
| reference | 0 | 1 |
| B | 1.4 | 2.1 |
| B | 9.8 | 6.4 |

Compound 4

| Composition type | PEO concentration % by weight | Relative permeation |
|---|---|---|
| reference | 0 | 1 |
| B | 7.5 | 16.4 |
| B | 9.8 | 27.6 |

Compound 5

| Composition type | PEO concentration % by weight | Relative permeation |
|---|---|---|
| reference | 0 | 1 |
| A | 4.7 | 4.1 |
| B | 3.1 | 6.0 |
| B | 4.1 | 6.7 |
| B | 5.0 | 10.7 |
| B | 7.5 | 18.7 |
| B | 9.8 | 37.2 |

Compound 6

| Composition type | PEO concentration % by weight | Relative permeation |
|---|---|---|
| reference | 0 | 1 |
| A | 4.7 | 2.9 |
| A | 5.3 | 5.9 |

The permeation tests performed show that an increasing concentration of PEO in the membrane increased the the permeation rate for each composition type and for each drug tested.

Tests of the Release of Drugs from the Devices (Implants or IUD:s)

The release rate of the drug from the implant or IUD was measured in vitro as follows:

The implants or IUD:s were attached into a stainless steel holder in vertical position and the holders with the implants were placed into glass bottles containing 75 ml of a dissolution medium. The glass bottles were shaken in shaking waterbath 100 rpm at 37° C. The dissolution medium was withdrawn and replaced by a fresh dissolution medium at predetermined time intervals, and the released drug was analysed by HPLC. The concentration of the dissolution medium and the moment of change (withdrawal and replacement) of medium were selected so that sink-conditions were maintained during the test.

The daily in vitro release of the drug from the devices are shown in FIGS. 1 to 5. The experiments demonstrate clearly the increased release rate when using for the matrix and membrane an elastomer composition with poly(alkylene oxide) groups in the polysiloxane.

It will be appreciated that the methods of the present invention can be incorporated in the form of a variety of embodiments, only a few of which are disclosed herein. It will be apparent for the specialist in the field that other embodiments exist and do not depart from the spirit of the invention. Thus, the described embodiments are illustrative and should not be construed as restrictive.

What is claimed is:

1. A device for the controlled release over a prolonged period of time of a drug having antiprogestinic properties, said device comprising a core comprising said drug and optionally a membrane encasing said core, said core and/or membrane being made of a siloxane-based elastomer composition comprising at least one elastomer and optionally a non-crosslinked polymer, wherein said elastomer composition comprises poly(alkylene oxide) groups and the poly(alkylene oxide) groups are present in the elastomer or polymer as alkoxy-terminated grafts of polysiloxane units, or as blocks, the said grafts or blocks being linked to the polysiloxane units by silicon-carbon bonds, or as a mixture of these forms, said poly(alkylene oxide) groups having the formula

where R is hydrogen or lower alkyl, $R_3$ is a linear or branched $C_2$–$C_6$ alkylene group and m is from 1 to 3.

2. The device according to claim 1, wherein the core is an elastomer matrix, optionally made of said elastomer composition.

3. The device according to claim 2, wherein the membrane or matrix is made of an elastomer based on polysiloxane units which comprise poly(alkylene oxide) groups.

4. The device according to claim 1, wherein in the elastomer composition the poly(alkylene oxide) groups are poly(ethylene oxide) groups (PEO groups).

5. The device according to claim 1, wherein the formula of the polysiloxane groups is

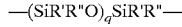

where some of the substituents R' and R" are
free groups which are the same or different and which are a lower alkyl group or a phenyl group in which case the said alkyl group may be substituted or unsubstituted, or alkoxy terminated poly(alkylene oxide) groups having the formula $-R_3-O-(CHRCH_2O)_m$-alk, where alk is a lower alkyl group, R is hydrogen or lower alkyl, $R_3$ is a linear or branched $C_2$–$C_6$ alkylene and m is 1 to 30,
bonds formed from the hydrogen or alkenyl groups to other polymer chains in the elastomer, and
optionally unreacted groups selected from the group consisting of hydrogen, vinyl and vinyl-terminated alkenyl, and
q is 1 to 3000.

6. The device according to claim 5, wherein the free R' and R" groups are lower alkyl groups.

7. The device according to claim 1, wherein the poly(alkylene oxide) groups are present in the elastomer in the form of poly(alkylene oxide) blocks having the formula

or

where R is hydrogen, a lower alkyl or phenyl, $R_1$ is hydrogen or lower alkyl, $R_3$ and $R_4$ are the same or different and are linear or branched $C_2$–$C_6$ alkylene and m is 1 to 30.

8. The device according to claim 1, wherein the elastomer composition is made up of two elastomers interlaced one inside the other, in which case
the first elastomer comprises poly(alkylene oxide) groups and that the poly(alkylene oxide) groups are present in the said elastomer as alkoxy-terminated grafts of polysiloxane units, or as blocks in which case the said grafts or blocks are linked to the polysiloxane units by silicon carbon bonds, or as a mixture of these forms, and that
the second elastomer is a siloxane elastomer.

9. The device according to claim 8, wherein the second elastomer is a poly(dimethyl siloxane) elastomer which optionally comprises poly(alkylene oxide) groups.

10. The device according to claim 9, wherein said second poly(dimethyl siloxane) elastomer contains poly(alkylene oxide) groups, which are present in the form of alkoxy-terminated grafts of poly(dimethyl siloxane) units, or as blocks in which case the said grafts or blocks are linked to the poly(dimethyl siloxane) units by silicon carbon bonds, or as a mixture of these forms.

11. The device according to claim 1, wherein the elastomer composition is a blend, which comprises
a siloxane elastomer and
a linear polysiloxane copolymer which comprises poly(alkylene oxide) groups in which case the poly(alkylene oxide) groups are present in the said polymer as alkoxy-terminated grafts of polysiloxane units, or as blocks in which case the said grafts or blocks are linked to the polysiloxane units by silicon carbon bonds, or as a mixture of these forms.

12. The device according to claim 2, wherein the matrix is encased in a membrane.

13. The device according to claim 12, wherein the matrix and the membrane both are made of an elastomer composition comprising poly(alkylene oxide) groups and the poly(alkylene oxide) groups are present in the elastomer or polymer as alkoxy-terminated grafts of polysiloxane units, or as blocks, the said grafts or blocks being linked to the polysiloxane units by silicon-carbon bonds or as a mixture of these forms.

14. The device according to claim 1, wherein the device is an implant, an intrauterine or intracervical device, an intravaginal device, or a transdermal patch.

15. The device according to claim 1, wherein the drug having antiprogestinic properties is a compound selected from a group consisting of 11beta-[(4-Dimethylamino)phenyl]-17beta-hydroxy-17alpha-(1-propinyl)-4,9-estradien-3-one (mifepristone);
11beta-[(4-Dimethylamino)phenyl]-17beta-hydroxy-17alpha-(1-propinyl)-18-homoestra-4,9-dien-3-one;
11beta-[(4-Dimethylamino)phenyl]-17beta-hydroxy-17alpha-(1-propinyl)-17a-homoestra-4,9,16-trien-3-one;
11beta-[(4-Dimethylamino)phenyl]-17alpha-hydroxy-17beta-(3-hydroxypropyl)-13α-methyl-estra-4,9-dien-3-one (onapristone);
(Z)-11beta-[(4-Dimethylamino)phenyl]-17beta-hydroxy-17alpha-(3-hydroxy-1-propenyl)estra-4,9-dien-3-one (lilopristone);
11beta-(4-Acetylphenyl)-17beta-hydroxy-17alpha-(1-propinyl)estra-4,9-dien-3-one;
(Z)beta-(4-Acetylphenyl)-17beta-hydroxy-17alpha-(3-hydroxy-1-propenyl)estra-4,9-dien-3-one;
11beta-(4-Methoxyphenyl)-17beta-hydroxy-17alpha-ethynyl-4,9-estradien-3-one;
(Z)-11beta-[(4-Dimethylamino)phenyl]-17beta-hydroxy-17alpha-(3-hydroxy-1-propenyl)estr-4-en-3-one;

4-[17β-Methoxy-17α-(methoxymethyl)-3-oxoestra-4,9-dien-11β-yl]benzaldehyde-1-(E)-oxime;

4-[17β-Hydroxy-17α-(methoxymethyl)-3-oxoestra-4,9-dien-11β-yl]benzaldehyde-1-(E)-oxime;

4-[17β-Methoxy-17α-(methoxymethyl)-3-oxoestra-4,9-dien-11β-yl]benzaldehyde-1-(E)-[O-(ethylamino)carbonyl]oxime;

4-[17β-Methoxy-17α-(methoxymethyl)-3-oxoestra-4,9-dien-11β-yl]benzaldehyde-1-(E)-[O-(ethoxy)carbonyl]oxime;

4-[17β-Methoxy-17α-(methoxymethyl)-3-oxoestra-4,9-dien-11β-yl]benzaldehyde-1-(E)-[O-(ethylthio)carbonyl]oxime;

4-[17β-Methoxy-17α-(ethoxymethyl)-3-oxoestra-4,9-dien-11β-yl]benzaldehyde-1-(E)-[O-(ethylthio)carbonyl]oxime;

4-[17β-Hydroxy-17α-(methoxymethyl)-3-oxoestra-4,9-dien-11β-yl]benzaldehyde-1-(E)-[O-(n-propylthio)carbonyl]oxime;

(Z)-6'-(4-cyanophenyl)-9,11α-dihydro-17beta-hydroxy-17α-[4-(1-oxo-3-methylbutoxy)-1-butenyl]-4'H-naphtho[3',2',1';10,9,11]estra-4-en-3-one;

(Z)-6'-(4-cyanophenyl)-9,11α-dihydro-17beta-hydroxy-17α-[3-(1-oxo-3-methylbutoxy)-1-propenyl]-4'H-naphtho[3',2',1';10,9,11]estra-4,15-dien-3-one;

(Z)-6'-(4-cyanophenyl)-9,11α-dihydro-17beta-hydroxy-17α-(3-hydroxy-1-propenyl)-4'H-naphtho[3',2',1';10,9,11]estra-4,15-dien-3-one;

(Z)-6'-(3-pyridinyl)-9,11α-dihydro-17beta-hydroxy-17α-(3-hydroxy-1-propenyl)-4'H-naphtho[3',2',1';10,9,11]estra-4,15-dien-3-one;

11β-(4-Acetylphenyl)-17β-hydroxy-17α-(1,1,2,2,2-pentafluoroethyl)estra-4,9-dien-3-one;

6'-(Acetyloxy)-9,11α-dihydro-17β-hydroxy-17α-(1,1,2,2,2-pentafluoroethyl)-4'H-naphth[3',2,',1':10,9,11]estr-4-en-3-one;

9,11α-(Dihydro)-17β-hydroxy-6'-(hydroxymethyl)-17α-(1,1,2,2,2-pentafluoroethyl)-4'H-naphth[3',2,',1':10,9,11]estr-4-en-3-one;

11beta-(4-Acetylphenyl)-19,24-dinor-17,23-epoxy-17alpha-chola-4,9,20-trien-3-one;

11beta-(4-Methoxyphenyl)-19,24-dinor-17,23-epoxy-17alpha-chola-4,9,20-trien-3-one;

(Z)-11beta,19-[4-(3-Pyridinyl)-o-phenylene)]-17beta-hydroxy-17α-[3-hydroxy-1-propenyl]-4-androsten-3-one;

(Z)-11beta,19-[4-(4-Cyanophenyl-o-phenylene)]-17beta-hydroxy-17α-[3-hydroxy-1-propenyl]-4-androsten-3-one;

11beta-[4-(1-methylethenyl)phenyl]-17α-hydroxy-17beta-(3-hydroxypropyl)-13α-estra-4,9-dien-3-one;

11beta-[4-(3-Furanyl)phenyl]-17α-hydroxy-17beta-(3-hydroxypropyl)-13α-estra-4,9-dien-3-one;

4',5'-Dihydro-11beta-[4-(dimethylamino)phenyl]-6beta-methylspiro[estra-4,9-dien-17beta,2'(3'H)-furan]-3-one;

4',5'-Dihydro-11beta-[4-(dimethylamino)phenyl]-7beta-methylspiro[estra-4,9-dien-17beta,2'(3'H)-furan]-3-one;

4-beta,17α-Dimethyl-17beta-hydroxy-3-oxo-4α,5-epoxy-5α-androstan-2α-carbonitrile;

7α-[9-(4,4,5,5,5-Pentafluoropentyl)sulfinyl]nonyl]estra-1,3,5(10)-trien-3,17 beta-diol;

3-(4-chloro-3-trifluoromethylphenyl)-1-(4-iodobenzenesulfonyl)-1,4,5,6-tetrahydropyridazine;

(R,S)3-(4-chloro-3-trifluoromethylphenyl)-1-(iodobenzenesulfonyl)-6-methyl-1,4,5,6-tetrahyropyridazine;

3-(3,4-dichlorophenyl)1-(3,5-dichlorobenzoyl)-1,4,5,6-tetrahydropyridazine;

3-(3,4-dichlorophenyl)1-(2,5-dichlorobenzenesulfonyl)-1,4,5,6-tetrahydropyridazine;

7,8-Dibromo-3,4-diazo-1,2,3,10,10a-hexahydro-3-(4-iodobenzenesulfonyl)-phenanthrene; and 7Chloro-3,4-diazo-1,2,3,9,10,10a-hexahydro-3-(2,5-dichlorobenzenesulfonyl)-phenanthrene.

\* \* \* \* \*